(12) United States Patent
Tachibana et al.

(10) Patent No.: US 10,332,734 B2
(45) Date of Patent: Jun. 25, 2019

(54) SAMPLE PLATE FOR MASS SPECTROMETRIC ANALYSIS, MASS SPECTROMETRIC ANALYSIS METHOD, AND MASS SPECTROMETRIC ANALYSIS DEVICE

(71) Applicant: AGC Inc., Chiyoda-ku (JP)

(72) Inventors: Yuko Tachibana, Chiyoda-ku (JP); Yoji Nakajima, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 15/799,263

(22) Filed: Oct. 31, 2017

(65) Prior Publication Data

US 2018/0053643 A1 Feb. 22, 2018

Related U.S. Application Data

(63) Continuation of application No. PCT/JP2016/063676, filed on May 6, 2016.

(30) Foreign Application Priority Data

May 8, 2015 (JP) .................................. 2015-095363

(51) Int. Cl.
*H01J 49/04* (2006.01)
*H01J 27/24* (2006.01)
(Continued)

(52) U.S. Cl.
CPC .......... *H01J 49/0418* (2013.01); *G01N 27/62* (2013.01); *G01N 27/64* (2013.01); *H01J 49/164* (2013.01)

(58) Field of Classification Search
None
See application file for complete search history.

(56) References Cited

U.S. PATENT DOCUMENTS

| 5,304,344 A * | 4/1994 | Huang ................... C22C 14/00 420/418 |
| 6,040,056 A * | 3/2000 | Anzaki ................... C03C 17/36 428/432 |

(Continued)

FOREIGN PATENT DOCUMENTS

| JP | 2007-263600 | 10/2007 |
| JP | 2009-81055 | 4/2009 |

(Continued)

OTHER PUBLICATIONS

Lai-Rowcroft, "Novel surfaces for MALDI-MS", A thesis submitted to the Universit of Manchester for the degree of PhD in Chemstry in the Faculty of Engineering and Physical Science (Year: 2012).*

(Continued)

*Primary Examiner* — Michael J Logie
(74) *Attorney, Agent, or Firm* — Oblon, McClelland, Maier & Neustadt, L.L.P.

(57) ABSTRACT

Provided is a sample plate for mass spectrometric analysis, which comprises a substrate and a metal thin film formed on the substrate. The metal thin film contains Ag, Al or Cu as the main component and further contains a specific additive element $M_{Ag}$, $M_{Al}$ or $M_{Cu}$ depending on the element as the main component, in a ratio ($M_{Ag}$/Ag) of the total number of atoms of the additive element $M_{Ag}$ to the number of atoms of Ag of from 0.001 to 0.5, a ratio ($M_{Al}$/Al) of the total number of atoms of the additive element $M_{Al}$ to the number of atoms of Al of from 0.001 to 0.5, or a ratio ($M_{Cu}$/Cu) of the total number of atoms of the additive element $M_{Cu}$ to the number of atoms of Cu of from 0.001 to 0.5.

14 Claims, 18 Drawing Sheets

(51) Int. Cl.
*H01J 49/16* (2006.01)
*G01N 27/62* (2006.01)
*G01N 27/64* (2006.01)

(56) References Cited

U.S. PATENT DOCUMENTS

| | | | |
|---|---|---|---|
| 2004/0094705 A1* | 5/2004 | Wood | H01J 49/0418 250/288 |
| 2008/0135781 A1* | 6/2008 | Miyata | H01J 49/0418 250/489 |
| 2008/0139998 A1* | 6/2008 | Silver | A01N 25/34 604/74 |
| 2010/0065735 A1 | 3/2010 | Murakami et al. | |
| 2012/0104243 A1* | 5/2012 | Verbeck, IV | H01J 49/0418 250/282 |
| 2013/0157896 A1 | 6/2013 | Cheng et al. | |
| 2015/0075998 A1* | 3/2015 | Cooks | C25C 7/00 205/568 |
| 2015/0160377 A1* | 6/2015 | Kuroda | G02B 1/118 428/141 |
| 2018/0211794 A1* | 7/2018 | Brambilla | H01G 11/56 |

FOREIGN PATENT DOCUMENTS

| | | |
|---|---|---|
| JP | 2010-71727 | 4/2010 |
| JP | 2012-7891 | 1/2012 |
| JP | 4911704 | 4/2012 |
| JP | 2012-207954 | 10/2012 |
| JP | 5068206 | 11/2012 |
| JP | 5078456 | 11/2012 |
| JP | 5317054 | 10/2013 |
| JP | 2015-179617 | 10/2015 |
| WO | WO 2014/027447 A1 | 2/2014 |

OTHER PUBLICATIONS

Mabott et al., "The optimization of Facile substrates for surface enhanced Raman scatterin through galvanic replacement of silver onto copper" (Year: 2012).*

Mabott et al., "Supplementary Information The optimization of Facile substrates for surface enhanced Raman scattering through galvanic replacement of silver onto copper" (Year: 2012).*

International Search Report dated Jul. 19, 2016 in PCT/JP2016/063676, filed on May 6, 2016.

Tetsu Yonezawa et al. "Detailed Investigation on the Possibility of Nanoparticles of Various Metal Elements for Surface-Assisted Laser Desorption/Ionization Mass Spectrometry," Analytical Sciences, Mar. 2009, vol. 25, 2009, pp. 8.

Yuko Tachibana et al. "Optical properties of multilayers composed of silver and dielectric materials," Thin Solid Films 442, 2003, pp. 5.

Jing Wei et al. "Desorption-ionization mass spectrometry on porous silicon," Nature, vol. 399, May 20, 1999, pp. 4.

Grade et al, "Secondary Ion Mass Spectrometry, Cationization of Organic Molecules with Metals", *J. Am. Chem. Soc,* 1978, vol. 100, No. 18, pp. 5615-5621.

* cited by examiner

SAMPLE PLATE FOR MASS SPECTROMETRIC ANALYSIS, MASS SPECTROMETRIC ANALYSIS METHOD, AND MASS SPECTROMETRIC ANALYSIS DEVICE

TECHNICAL FIELD

The present invention relates to a sample plate for mass spectrometric analysis, a mass spectrometric analysis method using the sample plate, and a mass spectrometric analysis device provided with the sample plate.

BACKGROUND ART

Laser desorption/ionization mass spectrometry (hereinafter sometimes referred to as LDI-MS) is a method for carrying out mass spectrometric analysis of a sample by applying a laser to a sample to cause vaporization and ionization of sample molecules, detecting the ionized sample molecules by a detector and measuring the mass-to-charge ratio (m/z).

As LDI-MS, matrix-assisted laser desorption/ionization mass spectrometry (hereinafter sometimes referred to as MALDI-MS) has been known in which a sample is mixed with a matrix (for example, a low molecular weight organic compound) as an ionization-assisting substance and a cationizing agent, the mixture is irradiated with a laser, and sample molecules are vaporized by a heat energy generated by the matrix absorbing the laser while decomposition of the sample molecules is suppressed, and at the same time, the sample molecules are cationized by cations derived from the cationizing agent.

However, in the case of MALDI-MS, in a mass spectrum indicating the signal intensity by the y-axis and m/z by the x-axis, not only peaks derived from the sample but also peak derived from the matrix are observed, and the peaks derived from the sample can hardly be distinguished.

As LDI-MS not employing a matrix, surface-assisted laser desorption/ionization mass spectrometry (hereinafter sometimes referred to as SALDI-MS) has been developed in which a sample is placed on a sample plate having a surface which can exhibit an ionization-assisting effect, and by a thermal energy generated by the sample plate absorbing the laser, sample molecules are vaporized and cationized.

As a sample plate used in SALDI-MS, for example, the following have been proposed.

(1) A porous silicon plate having pores with a size of several hundreds nm, formed by electrolytic etching (Non-Patent Document 1).

(2) A sample plate formed by dropping a liquid containing Pt nanoparticles or Au nanoparticles on the surface of a commercially available LDI plate formed of e.g. stainless steel, followed by drying so that the nanoparticles are supported (Non-Patent Document 2, Patent Document 7).

(3) A sample plate having e.g. a metal thin film formed on the surface of a substrate having microstructures such as porous structures on its surface (Patent Documents 1 to 4).

(4) A sample plate having metal nanostructures (such as metal nanorods or dendritic platinum nanostructures) formed on the surface of a substrate (Patent Documents 5 and 6).

(5) A sample plate formed by dropping a liquid containing an oxide powder of Fe or Co on the surface of a substrate, followed by drying, so that nanoparticles are supported (Patent Document 8).

PRIOR ART DOCUMENTS

Patent Documents

Patent Document 1: JP-A-2007-263600
Patent Document 2: Japanese Patent No. 5,078,456
Patent Document 3: WO2014/027447
Patent Document 4: Japanese Patent No. 5,068,206
Patent Document 5: JP-A-2012-207954
Patent Document 6: JP-A-2012-007891
Patent Document 7: Japanese Patent No. 4,911,704
Patent Document 8: Japanese Patent No. 5,317,054

Non-Patent Documents

Non-Patent Document 1: J. Wei, et al., Nature, 1999, vol. 399, p. 243-246
Non-Patent Document 2: T. Yonezawa, et al., Analytical Sciences, March 2009, vol. 25, p. 339-346

DISCLOSURE OF INVENTION

Technical Problem

However, the sample plate (1) has a problem such that since the porous silicon on its surface is easily oxidized, the ionization-assisting effect will remarkably decrease in a short time. Accordingly, as time passes after preparation of the sample, peaks derived from the sample will not sufficiently be detected in a mass spectrum.

The sample plate (2) has a problem such that due to dispersion of the in-plane distribution of the nanoparticles on the surface, the ionization-assisting effect is also dispersed in the plane. Accordingly, in the case of carrying out imaging mass spectrometry (hereinafter sometimes referred to as IMS) for two-dimensionally obtaining distribution or the like of an analyte in the sample (e.g. biological body tissue), accurate distribution or the like of the analyte may not be obtained.

Further, since a noble metal itself such as Pt or Au cannot cationize the sample molecules, in the case of using the sample plate (2), it is necessary to use a cationizing agent in combination, or it is necessary to rely on a very small amount of cations (such as Na+) which adhere to the sample or its vicinity e.g. by surface contamination.

However, in a case where a cationizing agent is used in combination, the in-plane distribution of the cationizing agent on the surface of the sample is also dispersed. Accordingly, in a case of carrying out IMS, accurate distribution or the like of the analyte may not be obtained. On the other hand, in a case where a very small amount of cations which adhere to the sample or its vicinity are relied on, the efficiency of cationization of the sample molecules tends to be poor. Accordingly, peaks derived from the sample may not sufficiently be detected in a mass spectrum.

Further, it is reported in Non-Patent Document 2 that no ionization-assisting effect of the Ag nanoparticles and the Cu nanoparticles is confirmed.

The sample plate (3) cannot easily be produced since formation of microstructures such as porous structures on the surface of the substrate is necessary. Further, in a case where the metal thin film is a film of a noble metal such as Pt or Au, the sample plate (3) has the same problem as the sample plate (2). Further, in a case where the metal thin film is a film of e.g. Ag or Cu, the ionization-assisting effect is estimated to be insufficient based on the report by Non-Patent Document 2.

The sample plate (4) cannot easily be produced since formation of metal nanostructures on the surface of a substrate is necessary. Further, in a case where the metal nanostructures are structures of a noble metal such as Pt or Au, the sample plate (4) has the same problem as the sample plate (2). Further, in a case where the metal nanostructures are structures of e.g. Ag or Cu, the ionization-assisting effect is estimated to be insufficient from the report by Non-Patent Document 2.

Since the sample plate (5) is obtained by applying a dispersion liquid having nanoparticles dispersed, followed by drying, dispersion of the in-plane distribution of the nanoparticles is inevitable like the sample plate (2), and a problem of in-plane dispersion of the ionization-assisting effect is estimated.

Under these circumstances, it is an object of the present invention to provide a sample plate for mass spectrometric analysis which requires no use of a matrix in combination, of which the ionization-assisting effect will hardly decrease with the lapse of time, of which in-plane dispersion of the ionization-assisting effect is small, with which a favorable efficiency of formation of cationized sample molecules is achieved without separately using a cationizing agent in combination, and which can easily be produced; and a mass spectrometric analysis method and a mass spectrometric analysis device by which peaks derived from the sample are sufficiently detected in a mass spectrum and the peaks derived from the sample can easily be distinguished, and by which accurate distribution or the like of the analyte can be obtained by IMS.

Solution to Problems

The present invention has the following aspects.

[1] A sample plate for mass spectrometric analysis, which comprises a substrate and a metal thin film formed on the substrate, wherein the metal thin film is any one of the following (A) to (C):

(A) a metal thin film containing Ag and at least one additive element $M_{Ag}$ selected from the group consisting of Pd, Au, Pt, Ir, Cu, Al, Zn, Sn, Ni, Cr, Co, Zr, Si, Ti, Sb, Ga, Nd, Ge and Bi, in a ratio ($M_{Ag}$/Ag) of the total number of atoms of the additive element $M_{Ag}$ to the number of atoms of Ag in the metal thin film of from 0.001 to 0.5;

(B) a metal thin film containing Al and at least one additive element $M_{Al}$ selected from the group consisting of Nd, Cu, Si, Mg, Cr, Mn, Zn, Fe, Ta, Ni, La, Ge, Ga, Ag, Au, Pd, Pt, Ir and Ti, in a ratio ($M_{Al}$/Al) of the total number of atoms of the additive element $M_{Al}$ to the number of atoms of Al in the metal thin film of from 0.001 to 0.5;

(C) a metal thin film containing Cu and at least one additive element $M_{Cu}$ selected from the group consisting of Sn, Zn, Pb, Ni, Al, Fe, Mn, Au, Ti, Cr, Mg, Si, In, Ga, Se, Ca, Ag, Au, Pd, Pt, Ir and P, in a ratio ($M_{Cu}$/Cu) of the total number of atoms of the additive element $M_{Cu}$ to the number of atoms of Cu in the metal thin film of from 0.001 to 0.5.

[2] The sample plate for mass spectrometric analysis according to [1], wherein the ratio (O/Ag) of the number of atoms of O (oxygen) to the number of atoms of Ag in the metal thin film (A) is from 0 to 0.2.

[3] The sample plate for mass spectrometric analysis according to [1] or [2], wherein the resistivity of the metal thin film (A) is at most $1 \times 10^{-4}$ Ω·cm.

[4] The sample plate for mass spectrometric analysis according to any one of the above [1] to [3], wherein in an X-ray photoelectron spectrum of the surface of the metal thin film (A) obtained by X-ray photoelectron spectroscopy, the integrated intensity of a peak observed at a binding energy position higher by from 2.5 to 5 eV than the position (368 eV) of a peak derived from $Ag3d_{5/2}$ photoelectrons, is higher than 0.001, where the integrated intensity of the peak derived from $Ag3d_{5/2}$ photoelectrons is 1.

[5] The sample plate for mass spectrometric analysis according to the above [1], wherein the ratio (O/Al) of the number of atoms of O (oxygen) to the number of atoms of Al in the metal thin film (B) is from 0 to 1.5.

[6] The sample plate for mass spectrometric analysis according to the above [1] or [5], wherein the resistivity of the metal thin film (B) is at most $1 \times 10^{-3}$ Ω·cm.

[7] The sample plate for mass spectrometric analysis according to any one of [1], [5] and [6], wherein in an X-ray photoelectron spectrum of the surface of the metal thin film (B) obtained by X-ray photoelectron spectroscopy, the integrated intensity of a peak observed at a binding energy position higher by from 5 to 43 eV than the position (73 eV) of a peak derived from $Al2p_{3/2}$ photoelectrons, is higher than 0.01, where the integrated intensity of the peak derived from $Al2p_{3/2}$ photoelectrons is 1.

[8] The sample plate for mass spectrometric analysis according to the above [1], wherein the ratio (O/Cu) of the number of atoms of O (oxygen) to the number of atoms of Cu in the metal thin film (C) is from 0 to 0.3.

[9] The sample plate for mass spectrometric analysis according to the above [1] or [8], wherein the resistivity of the metal thin film (C) is at most $1 \times 10^{-3}$ Ω·cm.

[10] A mass spectrometric analysis method, which uses the sample plate for mass spectrometric analysis as defined in any one of the above [1] to [9].

[11] A mass spectrometric analysis device, which is provided with the sample plate for mass spectrometric analysis as defined in any one of the above [1] to [9].

Advantageous Effects of Invention

According to the sample plate for mass spectrometric analysis of the present invention, it is not necessary to use a matrix in combination, the ionization-assisting effect will hardly decrease with the lapse of time, the in-plane dispersion of the ionization-assisting effect tends to be small, a favorable efficiency of cationization of sample molecules is achieved without using a cationizing agent in combination, and such a sample plate can easily be produced.

According to the mass spectrometric analysis method and the mass spectrometric analysis device of the present invention, in a mass spectrum, peaks derived from a sample can sufficiently be detected, and the peaks derived from a sample can readily be distinguished, and accurate distribution or the like of an analyte can be obtained by IMS.

BRIEF DESCRIPTION OF DRAWINGS

FIG. 2-1 is a mass spectrum within a range of m/z of from 0 to 1,100 obtained by mass spectrometric analysis using the sample plate for mass spectrometric analysis in Ex. 1.

FIG. 2-2 is a mass spectrum within a range of m/z of from 350 to 1,100 obtained by mass spectrometric analysis using the sample plate for mass spectrometric analysis in Ex. 1.

FIG. 2-3 is a mass spectrum within a range of m/z of from 550 to 760 obtained by mass spectrometric analysis using the sample plate for mass spectrometric analysis in Ex. 1.

FIG. 3 is an X-ray photoelectron spectrum of a metal thin film of the sample plate for mass spectrometric analysis in Ex. 2.

FIG. 4-1 is mass spectra within a range of m/z of from 460 to 1,050 obtained by mass spectrometric analysis using the sample plates for mass spectrometric analysis in Ex. 1, 3 and 4.

FIG. 4-2 is mass spectra within a range of m/z of from 550 to 750 obtained by mass spectrometric analysis using the sample plates for mass spectrometric analysis in Ex. 1, 3 and 4.

FIG. 6-1 is a mass spectrum within a range of m/z of from 1,400 to 3,000 obtained by mass spectrometric analysis using the sample plate for mass spectrometric analysis in Ex. 6.

FIG. 6-2 is a mass spectrum within a range of m/z of from 1,900 to 2,230 obtained by mass spectrometric analysis using the sample plate for mass spectrometric analysis in Ex. 6.

FIG. 11-1 is an X-ray photoelectron spectrum of a metal thin film of the sample plate for mass spectrometric analysis in Ex. 17.

FIG. 11-2 is a mass spectrum obtained by mass spectrometric analysis using the sample plates for mass spectrometric analysis in Ex. 17.

DESCRIPTION OF EMBODIMENTS

The following definitions of terms apply throughout the specification including Claims.

A "sample plate" means a member on which a sample is to be placed in a mass spectrometric analysis device.

"Ag" means Ag element unless otherwise specified, and is not limited to Ag metal simple substance. The same applies to other elements such as Al and Cu.

<Sample Plate for Mass Spectrometric Analysis>

The sample plate for mass spectrometric analysis of the present invention comprises a substrate and a metal thin film formed on the substrate.

Figure 1:
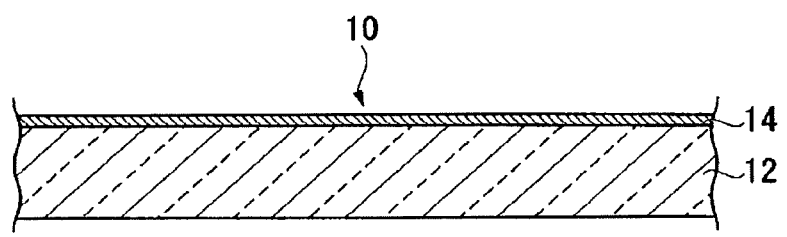
FIG. 1 is a cross sectional view illustrating an example of a sample plate for mass spectrometric analysis of the present invention.

FIG. 1 is a cross sectional view illustrating an example of the sample plate for mass spectrometric analysis of the present invention. A sample plate 10 for mass spectrometric analysis comprises a substrate 12 and a metal thin film 14 formed on one side of the substrate 12.

The visible light transmittance of the sample plate for mass spectrometric analysis of the present invention is preferably at least 50%, more preferably at least 70%, further preferably at least 80%. When the visible light transmittance of the sample plate for mass spectrometric analysis of the present invention is at least the lower limit value of the above range, observation with an optical microscope by backlight is possible. As a result, in IMS, both information on the form of a sample obtainable from optical images by an optical microscope and e.g. distribution of an analyte in the sample obtainable by mass spectrometric analysis can be utilized for analysis.

(Substrate)

As a material of the substrate, glass, a resin, a metal, a semiconductor or a ceramic may, for example, be mentioned.

The substrate is preferably a transparent substrate with a view to increasing the visible light transmittance of the sample plate for mass spectrometric analysis, and is particularly preferably a substrate made of glass. A glass substrate having a transparent electrically conductive film formed thereon may also be used.

The shape of the substrate is not particularly limited so long as a sample can be placed on it when the substrate is formed into a sample plate for mass spectrometric analysis.

(Metal Thin Film)

The metal thin film contains Ag, Al or Cu as the main component and further contains a specific additive element $M_{Ag}$, $M_{Al}$ or $M_{Cu}$ depending upon the element as the main component. Hereinafter $M_{Ag}$, $M_{Al}$ and $M_{Cu}$ will sometimes generally be referred to as M.

Ag, Al and Cu, which have a high ultraviolet absorptance, are expected to efficiently absorb an ultraviolet laser employed in LDI-MS and efficiently vaporize sample molecules. Further, Ag, Al and Cu, which are metals capable of generating the surface plasmon, are expected to improve the efficiency of formation of cationized sample molecules by the effect of the surface plasmon excited on the surface of the metal thin film. That is, electrons are captured by the localized electric field formed by the surface plasmon, and the electron density increases in the vicinity of the surface of the metal thin film, whereby an improvement of the probability of collision between electrons and neutral particles (Ag, Al or Cu), thus an improvement in the efficiency of formation of cations ($Ag^+$, $Al^+$ or $Cu^+$) and further an improvement in the efficiency of formation of the cationized sample molecules are expected.

However, Ag, Al or Cu simple substance is reported to have a low ionization-assisting effect as compared with Pt or Au. For example, Non-Patent Document 2 reports that no ionization-assisting effect is confirmed on Ag nanoparticles and Cu nanoparticles.

The present inventors have made extensive studies on reasons for this and as a result, found that Ag, Al or Cu simple substance is inferior in the moisture resistance and oxidation resistance, and its surface is thereby easily oxidized, and thus it has a low ionization-assisting effect.

Accordingly, in the present invention, the environmental resistance such as the moisture resistance and the oxidation resistance of Ag, Al or Cu is improved by adding a specific additive element M to Ag, Al or Cu, depending on each element. By such addition, a high ultraviolet absorptance and the effect of the surface plasmon which Ag, Al or Cu intrinsically has, are sufficiently achieved. As a result, a metal thin film containing Ag, Al or Cu as the main component and further containing a specific additive element M depending on the element as the main component, can efficiently absorb an ultraviolet laser employed in LDI-MS and efficiently vaporize sample molecules, and further, can improve the efficiency of formation of cationized sample molecules by the effect of the surface plasmon excited on the surface of the metal thin film.

Now, a first embodiment in which the main component of the metal thin film is Ag, a second embodiment in which the main component of the metal thin film is Al, and a third embodiment in which the main component of the metal thin film is Cu, will be described in detail.

First Embodiment

According to a first embodiment of the present invention, the sample plate for mass spectrometric analysis comprises a metal thin film containing Ag as the main component. The metal thin film contains Ag and at least one additive element $M_{Ag}$ selected from the group consisting of Pd, Au, Pt, Ir, Cu, Al, Zn, Sn, Ni, Cr, Co, Zr, Si, Ti, Sb, Ga, Nd, Ge and Bi. The metal thin film according to the first embodiment may contain O (oxygen).

In the first embodiment, the ratio ($M_{Ag}$/Ag) of the total number of atoms of the additive element $M_{Ag}$ to the number of atoms of Ag in the metal thin film is from 0.001 to 0.5, preferably from 0.005 to 0.25, more preferably from 0.01 to 0.15. When $M_{Ag}$/Ag is at most the upper limit value of the above range, the amount of Ag will be sufficient, and sample molecules can efficiently be vaporized and cationized. When $M_{Ag}$/Ag is at least the lower limit value of the above range, the environmental resistance such as the moisture resistance and the oxidation resistance of Ag can be improved by the additive element $M_{Ag}$. Accordingly, a high ultraviolet absorptance and the effect of the surface plasmon which Ag intrinsically has can be sufficiently achieved, and a sufficient ionization-assisting effect by the surface of the metal thin film can be achieved.

In the first embodiment, the ratio (O/Ag) of the number of atoms of O (oxygen) to the number of atoms of Ag in the metal thin film is preferably from 0 to 0.2, more preferably from 0 to 0.1, further preferably from 0 to 0.05. When O/Ag is at most the upper limit value of the above range, oxidation of Ag is suppressed. Accordingly, a high ultraviolet absorptance and the effect of the surface plasmon which Ag intrinsically has can further be achieved, and a higher ionization-assisting effect by the surface of the metal thin film can be achieved.

Whether Ag is in a metal state in the metal thin film in the first embodiment can be confirmed by a Ag3d photoelectron spectrum in an X-ray photoelectron spectrum of the surface of the metal thin film obtained by X-ray photoelectron spectroscopy. In a case where Ag is in a state of a metal not oxidized, a peak derived from $Ag3d_{5/2}$ photoelectrons is observed at a position with a binding energy of 368 eV. In a case where Ag is oxidized, the peak derived from $Ad3d_{5/2}$ photoelectrons shifts to the lower energy side by 0.3 eV ($Ag_2O$) or 0.6 eV (AgO). $I_{AlM}/I_{AlO}$, where $I_{AlM}$ is the integrated intensity of a component derived from the metal, and $I_{AlO}$ is the integrated intensity of a component derived from the oxide, of the peak derived from $Ag3d_{5/2}$ photoelectrons, is preferably from 0.5 to 1, more preferably from 0.8 to 1, further preferably from 0.9 to 1.

The resistivity of the metal thin film in the first embodiment is preferably at most $1\times10^{-4}$ Ω·cm, more preferably at most $5\times10^{-5}$ Ω·cm, further preferably at most $1\times10^{-5}$ Ω·cm. The resistivity of the metal thin film being at most the upper limit value of the above range means that oxidation of Ag is suppressed. Accordingly, a high ultraviolet absorptance and the effect of the surface plasmon which Ag intrinsically has can further be achieved, and a higher ionization-assisting effect by the surface of the metal thin film can be achieved.

Whether the metal thin film in the first embodiment achieves the effect of the surface plasmon can be confirmed by an X-ray photoelectron spectrum of the surface of the metal thin film obtained by X-ray photoelectron spectroscopy.

In a case where the metal thin film in the first embodiment achieves the effect of the surface plasmon, a peak is observed (hereinafter this peak will be referred to as $Ag3d_{5/2PL}$) at a binding energy position higher by from 2.5 to 5 eV than the position of a peak derived from $Ag3d_{5/2}$ photoelectrons. $Ag3d_{5/2PL}$ is considered to be a peak derived from $Ag3d_{5/2}$ photoelectrons the energy of which is lost by the Ag surface plasmon (surface plasmon loss peak), from the following document.

Non-Patent Document 3: Y. Tachibana, et al., Thin Solid Films 2003, vol. 442, p. 212-216

A higher peak integrated intensity of $Ag3d_{5/2PL}$ indicates a higher effect of the surface plasmon. Accordingly, the peak integrated intensity of $Ag3d_{5/2PL}$ is preferably higher than 0.001, more preferably higher than 0.005, further preferably higher than 0.01, where the integrated intensity of a peak derived from $Ag3d_{5/2}$ photoelectrons is 1.

The thickness of the metal thin film in the first embodiment is preferably from 0.1 to 20 nm, more preferably from 1 to 12 nm, further preferably from 5 to 7 nm. When the thickness of the metal thin film is at least the above lower limit value, the amount of Ag will be sufficient, and the cationized sample molecules can efficiently be formed. When the thickness of the metal thin film is at most the above upper limit value, the visible light transmittance of the sample plate for mass spectrometric analysis can be increased.

The above metal thin film according to the first embodiment corresponds to the metal thin film (A) in Claims of this application.

Second Embodiment

According to a second embodiment of the present invention, the sample plate for mass spectrometric analysis comprises a metal thin film containing Al as the main component. The metal thin film contains Al, and at least one additive element $M_{Al}$ selected from the group consisting of Nd, Cu, Si, Mg, Cr, Mn, Zn, Fe, Ta, Ni, La, Ge, Ga, Ag, Au, Pd, Pt, Ir and Ti. The metal thin film according to the second embodiment may contain O (oxygen).

In the second embodiment, the ratio ($M_{Al}$/Al) of the total number of atoms of the additive element $M_{Al}$ to the number of atoms of Al in the metal thin film is from 0.001 to 0.5, preferably from 0.005 to 0.25, more preferably from 0.01 to 0.15. When $M_{Al}$/Al is at most the upper limit value of the above range, the amount of Al will be sufficient, and sample molecules can efficiently be vaporized and cationized. When $M_{Al}$/Al is at least the lower limit value of the above range, the environmental resistance such as the moisture resistance and the oxidation resistance of Al can be improved by the additive element $M_{Al}$. Accordingly, a high ultraviolet absorptance and the effect of the surface plasmon which Al intrinsically has can be sufficiently achieved, and a sufficient ionization-assisting effect by the surface of the metal thin film can be achieved.

In the second embodiment, the ratio (O/Al) of the number of atoms of O (oxygen) to the number of atoms of Al in the metal thin film is preferably from 0 to 1.5, more preferably from 0 to 1, further preferably from 0 to 0.5.

The chemical bonding state of Al in the metal thin film in the second embodiment can be confirmed by an Al2p photoelectron spectrum in an X-ray photoelectron spectrum of the surface of the metal thin film obtained by X-ray photoelectron spectroscopy. In a case where Al is in a state of a metal not oxidized, a peak derived from Al2p$_{3/2}$ photoelectrons is observed at a position with a binding energy of 73 eV. In a case where Al is oxidized, the peak derived from Al2p$_{3/2}$ photoelectrons shifts to the higher energy side by about 3 eV. Since Al is a material which is easily oxidized, its outermost surface is oxidized by the time a film formed in vacuum is taken out to the air. Accordingly, even with an Al film having a low resistivity, both peak of a component derived from the metal and peak of a component derived from the oxide are observed as a peak derived from Al2p$_{3/2}$ photoelectrons in many cases. $I_{AlM}/I_{AlO}$, where $I_{AlM}$ is the integrated intensity of a component derived from the metal, and $I_{AlO}$ is the integrated intensity of a component derived from the oxide, of the peak derived from Al2p$_{3/2}$ photoelectrons, is preferably from 0.1 to 1, more preferably from 0.3 to 1, further preferably from 0.5 to 1.

When O/Al is at most the upper limit value of the above range and $I_{AlM}/I_{AlO}$ is at least the lower limit value of the above range, Al which is not oxidized is present in the vicinity of the surface. Accordingly, a high ultraviolet absorptance and the effect of the surface plasmon which Al intrinsically has can further be achieved, and a higher ionization-assisting effect by the surface of the metal thin film can be achieved.

The resistivity of the metal thin film in the second embodiment is preferably at most $1 \times 10^{-3}$ Ω·cm, more preferably at most $5 \times 10^{-5}$ Ω·cm, further preferably at most $1 \times 10^{-5}$ Ω·cm. The resistivity of the metal thin film being at most the upper limit value of the above range means that oxidation of Al is suppressed. Accordingly, a high ultraviolet absorptance and the effect of the surface plasmon which Al intrinsically has can further be achieved, and a higher ionization-assisting effect by the surface of the metal thin film can be achieved.

Whether the metal thin film in the second embodiment achieves the effect of the surface plasmon can be confirmed by an X-ray photoelectron spectrum of the surface of the metal thin film obtained by X-ray photoelectron spectroscopy.

In a case where the metal thin film in the second embodiment achieves the effect of the surface plasmon, a plasmon loss peak is observed (hereinafter this peak will be referred to as Al2p$_{3/2PL}$) at a binding energy position higher by from 5 to 43 eV than the position of a peak derived from Al2p$_{3/2}$ photoelectrons.

A higher peak integrated intensity of Al2p$_{3/2PL}$ indicates a higher effect of the surface plasmon. Accordingly, the peak integrated intensity of Al2p$_{3/2PL}$ is preferably higher than 0.01, more preferably higher than 0.05, further preferably higher than 0.1, where the integrated intensity of a peak derived from Al2p$_{3/2}$ photoelectrons is 1.

The thickness of the metal thin film in the second embodiment is preferably from 1 to 20 nm, more preferably from 5 to 12 nm, further preferably from 5 to 7 nm. When the thickness of the metal thin film is at least the above lower limit value, the amount of Al will be sufficient, and the sample molecules can efficiently be cationized. When the thickness of the metal thin film is at most the above upper limit value, the visible light transmittance of the sample plate for mass spectrometric analysis can be increased.

The above metal thin film according to the second embodiment corresponds to the metal thin film (B) in Claims of this application.

Third Embodiment

According to a third embodiment of the present invention, the sample plate for mass spectrometric analysis comprises a metal thin film containing Cu as the main component. The metal thin film contains Cu and at least one additive element $M_{Cu}$ selected from the group consisting of Sn, Zn, Pb, Ni, Al, Fe, Mn, Au, Ti, Cr, Mg, Si, In, Ga, Se, Ca, Ag, Au, Pd, Pt, Ir and P. The metal thin film according to the third embodiment may contain O (oxygen).

In the third embodiment, the ratio ($M_{Cu}$/Cu) of the total number of atoms of the additive element $M_{Cu}$ to the number of atoms of Cu in the metal thin film is from 0.001 to 0.5, preferably from 0.005 to 0.25, more preferably from 0.01 to 0.15. When $M_{Cu}$/Cu is at most the upper limit value of the above range, the amount of Cu will be sufficient, and sample molecules can efficiently be vaporized and cationized. When $M_{Cu}$/Cu is at least the lower limit value of the above range, the environmental resistance such as the moisture resistance and the oxidation resistance of Cu can be improved by the additive element $M_{Cu}$. Accordingly, a high ultraviolet absorptance and the effect of the surface plasmon which Cu intrinsically has can be sufficiently achieved, and a sufficient ionization-assisting effect by the surface of the metal thin film can be achieved.

In the third embodiment, the ratio (O/Cu) of the number of atoms of O (oxygen) to the number of atoms of Cu in the metal thin film is preferably from 0 to 0.3, more preferably from 0 to 0.2, further preferably from 0 to 0.1. When the ratio of O is at most the upper limit value of the above range, oxidation of Cu is suppressed. Accordingly, a high ultraviolet absorptance and the effect of the surface plasmon which Cu intrinsically has can further be achieved, and a higher ionization-assisting effect by the surface of the metal thin film can be achieved.

The resistivity of the metal thin film in the third embodiment is preferably at most $1 \times 10^{-3}$ Ω·cm, more preferably at most $5 \times 10^{-5}$ Ω·cm, further preferably at most $1 \times 10^{-5}$ Ω·cm. The resistivity of the metal thin film being at most the upper limit value of the above range means that oxidation of Cu is suppressed. Accordingly, a high ultraviolet absorptance and the effect of the surface plasmon which Cu intrinsically has can further be achieved, and a higher ionization-assisting effect by the surface of the metal thin film can be achieved.

The thickness of the metal thin film in the third embodiment is preferably from 1 to 20 nm, more preferably from 5 to 12 nm, further preferably from 5 to 7 nm. When the thickness of the metal thin film is at least the above lower limit value, the amount of Cu will be sufficient, and the sample molecules can more efficiently be cationized. When the thickness of the metal thin film is at most the above upper limit value, the visible light transmittance of the sample plate for mass spectrometric analysis can be increased.

The above metal thin film according to the third embodiment corresponds to the metal thin film (C) in Claims of this application.

(Method for Producing Sample Plate for Mass Spectrometric Analysis)

The sample plate for mass spectrometric analysis of the present invention is produced by forming a metal thin film on a substrate by a known film-forming method.

The film-forming method may, for example, be a physical deposition method (such as a sputtering method or a vacuum deposition method), and with a view to suppressing the amount of oxygen included in the metal thin film, it is preferably a physical deposition method, particularly preferably a sputtering method.

In a case where a metal thin film is formed by a physical deposition method, it is preferred to sufficiently remove residual gases in a vacuum chamber before film forming, from the following reasons.

As a vacuum chamber is evacuated with a vacuum pump, $N_2$ and $O_2$ which are major components in the air are removed, and the major residual gas in the vacuum chamber is $H_2O$. O and OH derived from the residual gas component are included in the metal thin film, and their amount depends on the amount of the residual gas in the vacuum chamber, that is, the degree of vacuum. For example, in a case where the ultimate vacuum degree in the vacuum chamber is $1\times10^{-1}$ Pa, the proportion of O in the metal thin film tends to be higher, and the resistivity tends to be higher.

In a case where the metal thin film is prepared by a sputtering method, it is preferred that the ultimate vacuum degree in the vacuum chamber is adjusted to be at most $5\times10^{-4}$ Pa, and then high purity Ar gas (purity of 99.99% or higher) is introduced to adjust the degree of vacuum to $1\times10^{-1}$ to 1 Pa, and a target metal material is sputtered by $Ar^+$. In such a manner, a metal thin film having a low proportion of O and having electrical conductivity close to that of a bulk material can be formed.

(Mechanism of Action)

The above-described sample plate for mass spectrometric analysis of the present invention comprises a substrate and a metal thin film formed on the substrate, wherein the metal thin film contains Ag, Al or Cu as the main component and contains a specific additive element M depending on the element as the main component in a specific ratio, and accordingly the environmental resistance such as the moisture resistance and the oxidation resistance of Ag, Al or Cu is improved. Accordingly, the metal thin film can efficiently absorb an ultraviolet laser employed in LDI-MS and can efficiently vaporize sample molecules. Accordingly, use of a matrix in combination is not necessary.

Further, since the environmental resistance such as the moisture resistance and the oxidation resistance of Ag, Al or Cu is improved, the ionization-assisting effect will hardly decrease with the lapse of time.

Further, since the environmental resistance such as the moisture resistance and the oxidation resistance of Ag, Al or Cu is improved, the effect of the surface plasmon excited on the surface of the metal thin film will sufficiently be achieved, and the efficiency of formation of cations will improve, and thus the efficiency of formation of cationized sample molecules will improve. Accordingly, a high efficiency of formation of cationized sample molecules will be achieved even without using a cationizing agent in combination.

In the sample plate having a metal thin film formed on its surface, the in-plane dispersion of the ionization-assisting effect tends to be small as compared with a sample plate having metal nanoparticles supported.

Further, a sample plate having a metal thin film formed on a substrate can easily be produced as compared with a sample plate having fine concave-convex structures formed on the surface of a substrate and a sample plate having metal nanostructures provided on the surface of a substrate.

Other Embodiment

The sample plate for mass spectrometric analysis of the present invention is not limited to the sample plate for mass spectrometric analysis shown in the drawing so long as it comprises a substrate and a metal thin film formed on the substrate, and the metal thin film contains Ag, Al or Cu as the main component and contains a specific additive element M depending on the element as the main component in a specific ratio. For example, it may have a layer containing a sample formed between the substrate and the metal thin film.

<Mass Spectrometric Analysis Method and Mass Spectrometric Analysis Device>

The mass spectrometric analysis method of the present invention is a method which uses the sample plate for mass spectrometric analysis of the present invention.

The mass spectrometric analysis device of the present invention is a device which is provide with the sample plate for mass spectrometric analysis of the present invention.

The sample plate for mass spectrometric analysis of the present invention is suitable for LDI-MS among the mass spectrometric analysis methods.

LDI-MS may, for example, be LDI-time-of-flight mass spectrometry (LDI-TOFMS), LDI-ion-trap MS, LDI-fourier transform MS, LDI-quadruple time-of-flight MS or time-of-flight connected MS, and is preferably LDI-TOFMS. For such analysis methods, a means known in SALDI-MS may be employed.

The mass spectrometric analysis device used for LDI-TOFMS may, for example, be one comprising a vacuum chamber, a sample plate placed in a vacuum chamber, a support table to support the sample plate, a light irradiation part to irradiate the sample plate with a ultraviolet laser, a flying direction controlling part to make cationized sample molecules desorbed from the sample on the sample plate fly toward a detector, and a detector.

(Mechanism of Action)

According to the above-described mass spectrometric analysis method and mass spectrometric analysis device of the present invention, which use the sample plate for mass spectrometric analysis of the present invention of which the ionization-assisting effect will hardly decrease with the lapse of time, and the efficiency of formation of cationized sample molecules is good without using a cationizing agent in combination, peaks derived from the sample can sufficiently be detected in a mass spectrum. Further, since the sample plate for mass spectrometric analysis of the present invention which requires no use of a matrix in combination, is used, peaks derived from the sample can easily be distinguished in a mass spectrum. Further, since the sample plate for mass spectrometric analysis of the present invention of which in-plane dispersion of the ionization-assisting effect is small, is used, an accurate distribution or the like of an analyte can be obtained by IMS.

EXAMPLES

Now, the present invention will be described in further detail with reference to Examples. However, it should be understood that the present invention is by no means restricted to the following specific description.

Ex. 1, 3, 4, 6 to 16 and 18 to 24 are Examples of the present invention, and Ex. 2, 5 and 17 are Reference Examples.

(Thickness)

The thickness of the metal thin film was measured by a surface profiler (manufactured by ULVAC, Inc., Dektak6M). At the time of forming the metal thin film, the substrate transport rate was adjusted to obtain a metal thin film having a desired thickness.

(Elemental Analysis)

The ratio of the total number of atoms of the additive elements to the number of atoms of the element as the main component on the surface of the metal thin film was calculated from the outermost surface composition measured by an X-ray photoelectron spectroscopy (manufactured by ULVAC-PHI, INCORPORATED, Quantera SXM). The ratio of the number of atoms of O (oxygen) to the number of atoms of the element as the main component was calculated from compositional analysis results at a point where no C1s peak was detected after surface organic contamination adsorbed on the outermost surface of the sample was removed by low acceleration $Ar^+$ ion beam sputtering in the X-ray photoelectron spectroscopy under the following conditions.

$Ar^+$ Ion beam accelerating voltage: 500 V
$Ar^+$ Ion beam scanning region: 2 mm×2 mm
$Ar^+$ Sputtering time: 1 to 1.5 minutes (Resistivity)

The resistivity of the metal thin film was obtained by multiplying the sheet resistivity of the metal thin film by the thickness of the metal thin film. The sheet resistance of the metal thin film was measured by the four-point probe method using a resistivity meter (manufactured by Mitsubishi Petrochemical, Loresta FP MCP-Tester).

(Visible Light Transmittance)

The visible light transmittance of the sample plate for mass spectrometric analysis was measured by a luminous transmittance meter (manufactured by Asahi Spectra Co., Ltd., Model 304).

(Measurement of Surface Plasmon)

The X-ray photoelectron spectrum of the surface of the metal thin film was measured by an X-ray photoelectron spectroscopy (manufactured by ULVAC-PHI, INCORPORATED, Quantera SXM).

In a case where the main component of the metal thin film was Ag, the integrated intensity of a peak ($Ag3d_{5/2PL}$) observed at a binding energy position higher by from 2.5 to 5 eV than a peak derived from $Ag3d_{5/2}$ photoelectrons, where the integrated intensity of the peak derived from $Ag3d_{5/2}$ photoelectrons was 1, was obtained.

(Mass Spectrometric Analysis)

As a mass spectrometric analysis device, a laser desorption/ionization time-of-flight mass spectrometer (manufactured by JEOL Ltd., JMS-S3000) was used.

The sample plate for mass spectrometric analysis provided with a sample, prepared in each Ex., was set in an engraved portion of a SUS target plate attached to the mass spectrometer. The target plate was placed in a vacuum chamber of the mass spectrometer, and mass spectrometric analysis was performed under the following conditions.

Irradiation light: Nd: YLF laser, wavelength: 349 nm (frequency: 1 kHz)
Radius of irradiation area: about 20 μm
Accelerating voltage: 20 kV
Measurement ion mode: positive ion mode
Delay Time: 300 nsec and 150 nsec
Grid voltage: 3 kV (Substrate)

As the substrate, a glass plate (manufactured by Asahi Glass Company, Limited, alkali-free glass, 15 mm×20 mm×0.5 mm in thickness) and a polyethylene terephthalate (hereinafter referred to as PET) film (manufactured by TOYOBO CO., LTD., A4300, 50 mm×50 mm×0.07 mm in thickness) were prepared.

(Sample)

Polyethylene glycol (PEG600) was dissolved in tetrahydrofuran to prepare a 1 mass % sample solution (1). Polyethylene glycol (PEG2000) was dissolved in tetrahydrofuran to prepare a 1 mass % sample solution (2). Further, Tinuvin (registered trademark) 292 (a mixture of bis(1,2,2,6,6-pentamethyl-4-piperidyl) sebacate and methyl 1,2,2,6,6-pentamethyl-4-piperidyl sebacate) was dissolved in tetrahydrofuran to prepare a 1 mass % sample solution (3).

Ex. 1

A glass plate was placed in a vacuum chamber of a magnetron sputtering apparatus (manufactured by BOC Industrial Gases, ILS-1600). The degree of vacuum in the vacuum chamber was adjusted to at most $1.3 \times 10^{-4}$ Pa, and high purity Ar gas (purity: 99.99 vol %) was introduced to adjust the degree of vacuum to $2 \times 10^{-1}$ Pa. A metal thin film (thickness: 14 nm) was formed on the surface of the glass plate by using an Ag target (432 mm×127 mm) containing 5 atomic % of Au, using an Ar gas as a sputtering gas and applying an electric power of 0.6 kw, to prepare a sample plate for mass spectrometric analysis. $M_{Ag}$/Ag, O/Ag, the thickness of the metal thin film, the sheet resistance, the resistivity, the visible light transmittance, and the integrated intensity of a peak of $Ag3d_{5/2PL}$ where the integrated intensity of a peak derived from $Ag3d_{5/2}$ photoelectrons was 1, are shown in Table 1.

Figures 1, 2:
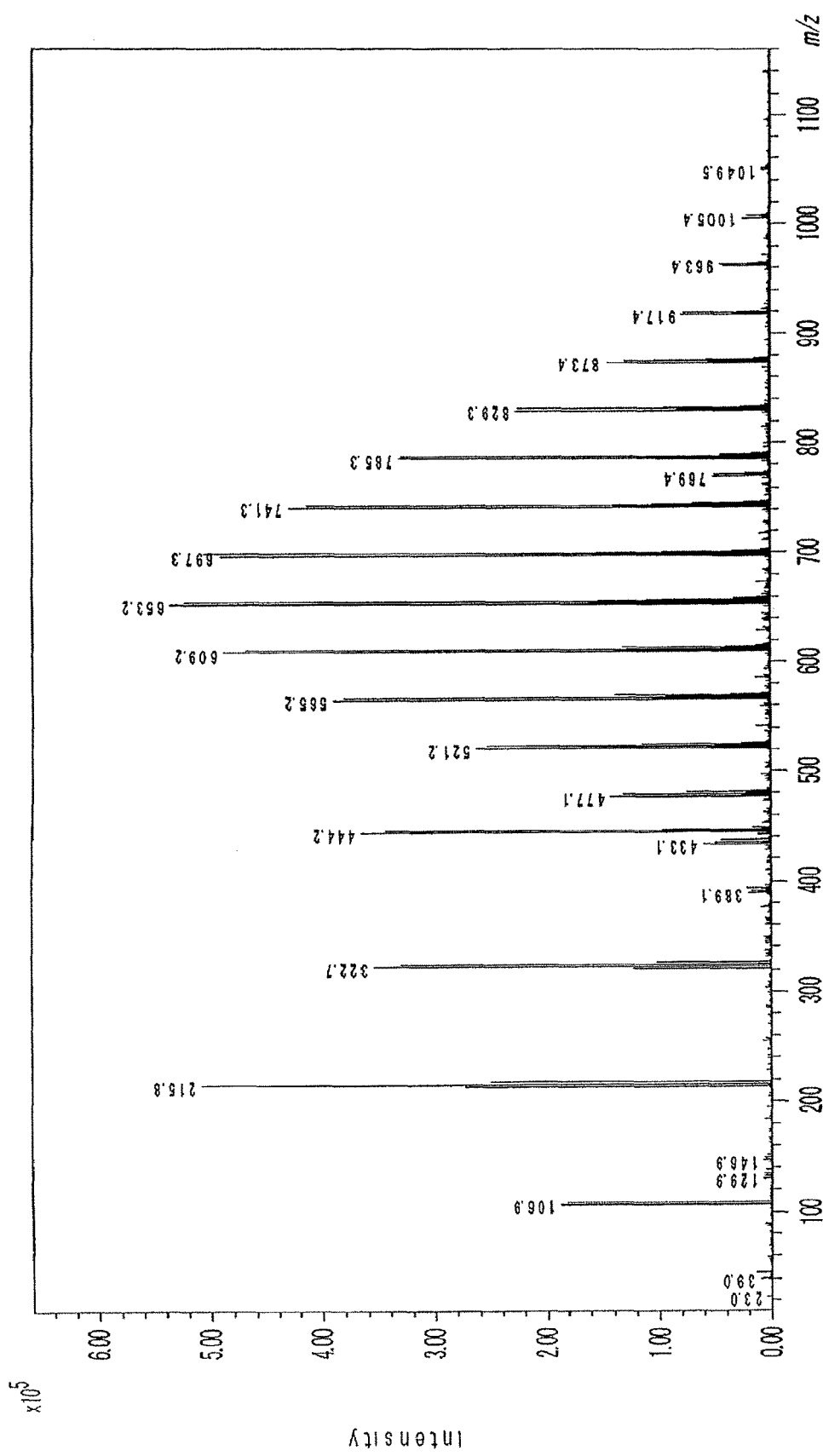
Figure 2:
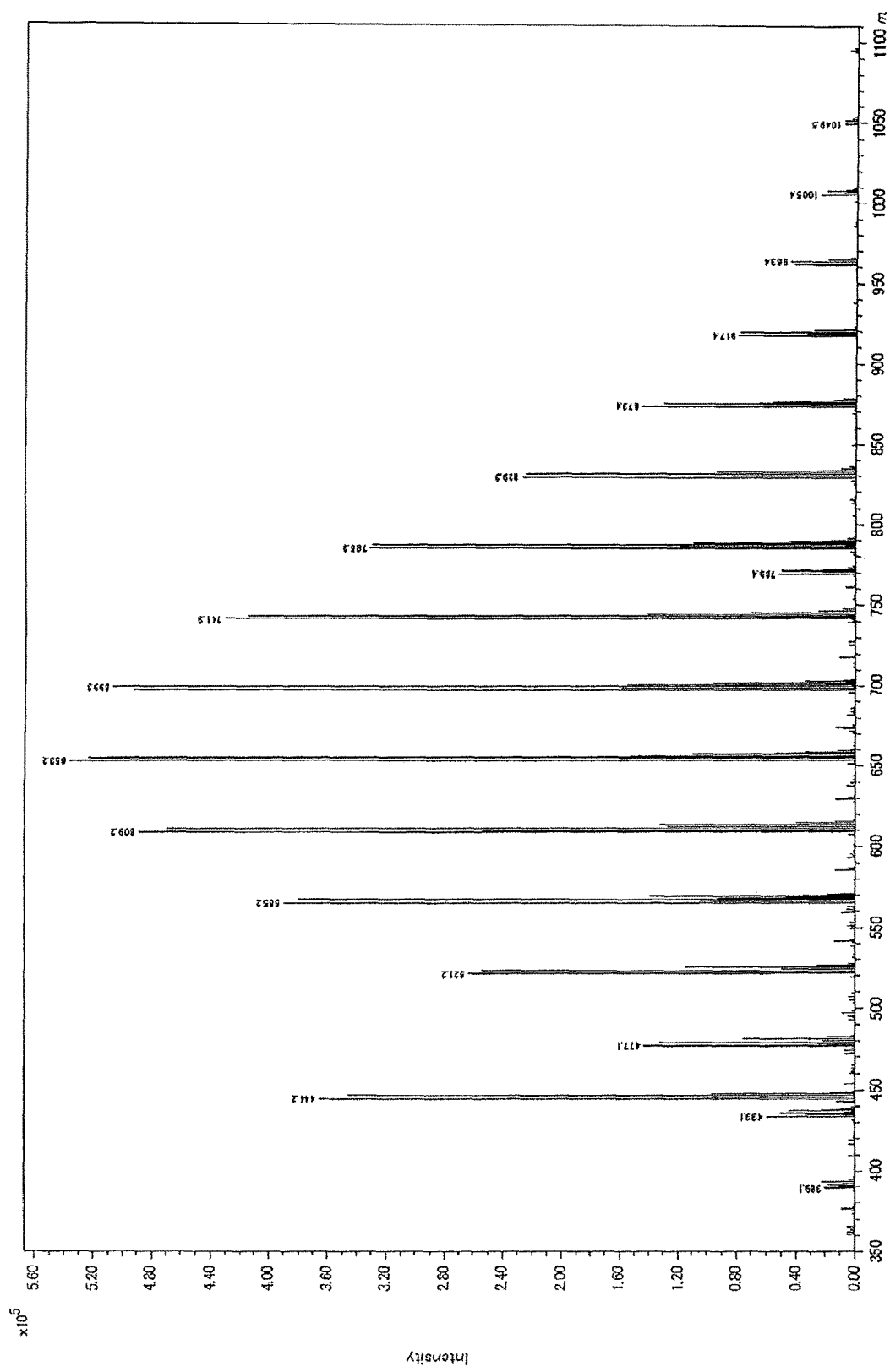
Figures 2, 3:
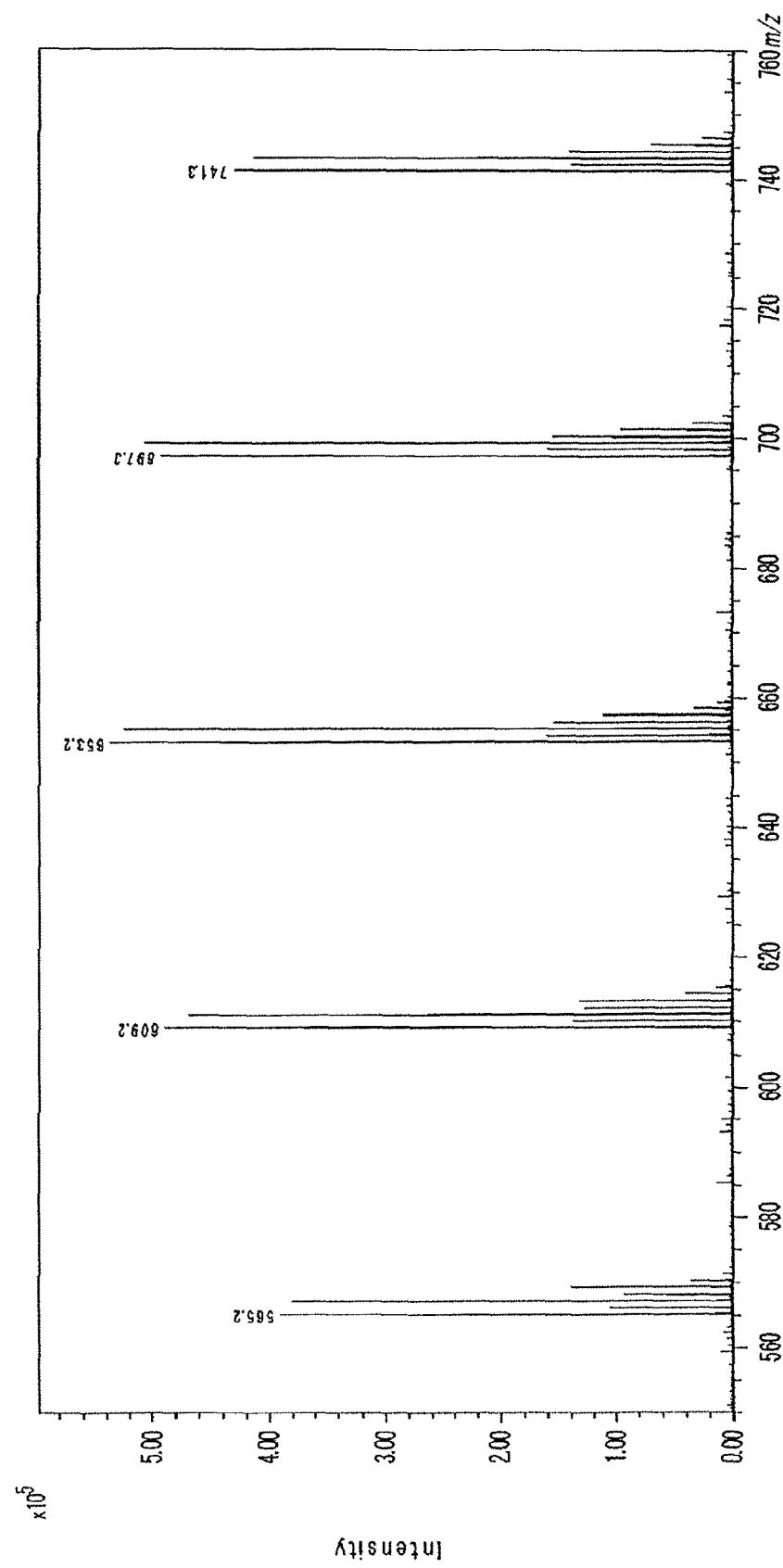
Figure 3:
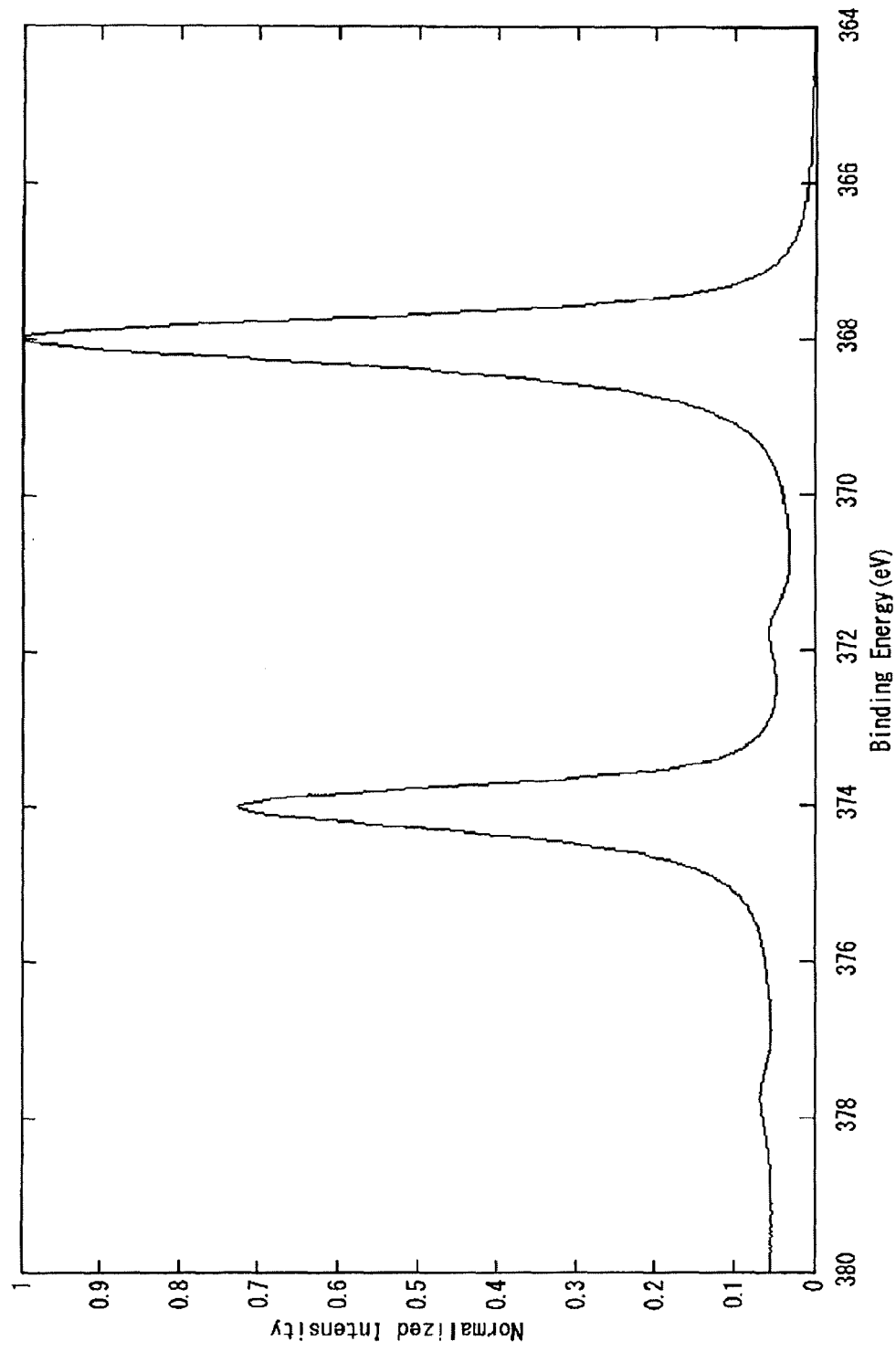

2 μL of the sample solution (1) was dropped on the surface of the metal thin film and dried to prepare a sample plate for mass spectrometric analysis provided with a sample, and mass spectrometric analysis was carried out. In this Ex., no matrix agent nor cationizing agent was used. The mass spectrum obtained by mass spectrometric analysis is shown in FIG. 2-1. Peaks derived from $Ag^+$ are observed at m/z 107 and m/z 109, and peaks derived from $Ag^+$-adduct sample molecules are observed at m/z of from 350 to 1,050, at the intervals, Δm/z 44 (derived from $CH_2CH_2O$) (see FIG. 2-2). Further, a mass spectrum (in detail) at m/z of from 550 to 760 is shown in FIG. 2-3. Peaks observed in the vicinity of m/z of 215, 323 and 444 are respectively derived from silver cluster ions $Ag_n^+$ (n=2, 3, 4). In the obtained mass spectrum, peaks other than the peaks derived from $Ag_n^+$ (n=2, 3, 4) are mainly peaks derived from $Ag^+$-adduct sample molecules, and a mass spectrum derived from the sample was clearly observed.

Ex. 2

The X-ray photoelectron spectrum of the surface of a metal thin film on a sample plate for mass spectrometric analysis prepared in the same manner as in Ex. 1 is shown in FIG. 3. The integrated intensity of a peak of $Ag3d_{5/2PL}$ was 0.07 where the integrated intensity of a peak derived from $Ag3d_{5/2}$ photoelectrons was 1.

Ex. 3

A glass plate was placed in a vacuum chamber of a magnetron sputtering apparatus (manufactured by Nisshin Seiki, JVS-S03). The degree of vacuum in the vacuum chamber was adjusted to at most $8 \times 10^{-4}$ Pa, and high purity Ar gas (purity: 99.99 vol %) was introduced to adjust the degree of vacuum to $2 \times 10^{-1}$ Pa. A metal thin film (thickness: 10 nm) was formed on the surface of the glass plate by using an Ag target (200 mm×70 mm) containing 1 atomic % of Bi and 0.2 atomic % of Nd, using an Ar gas as a sputtering gas and applying an electric power of 0.2 kw to prepare a sample plate for mass spectrometric analysis. $M_{Ag}$/Ag, O/Ag, the thickness of the metal thin film, the sheet resistance, the resistivity, the visible light transmittance and the integrated intensity of a peak of $Ag3d_{5/2PL}$ where the integrated intensity of a peak derived from $Ag3d_{5/2}$ photoelectrons was 1, are shown in Table 1.

Figures 1, 4:
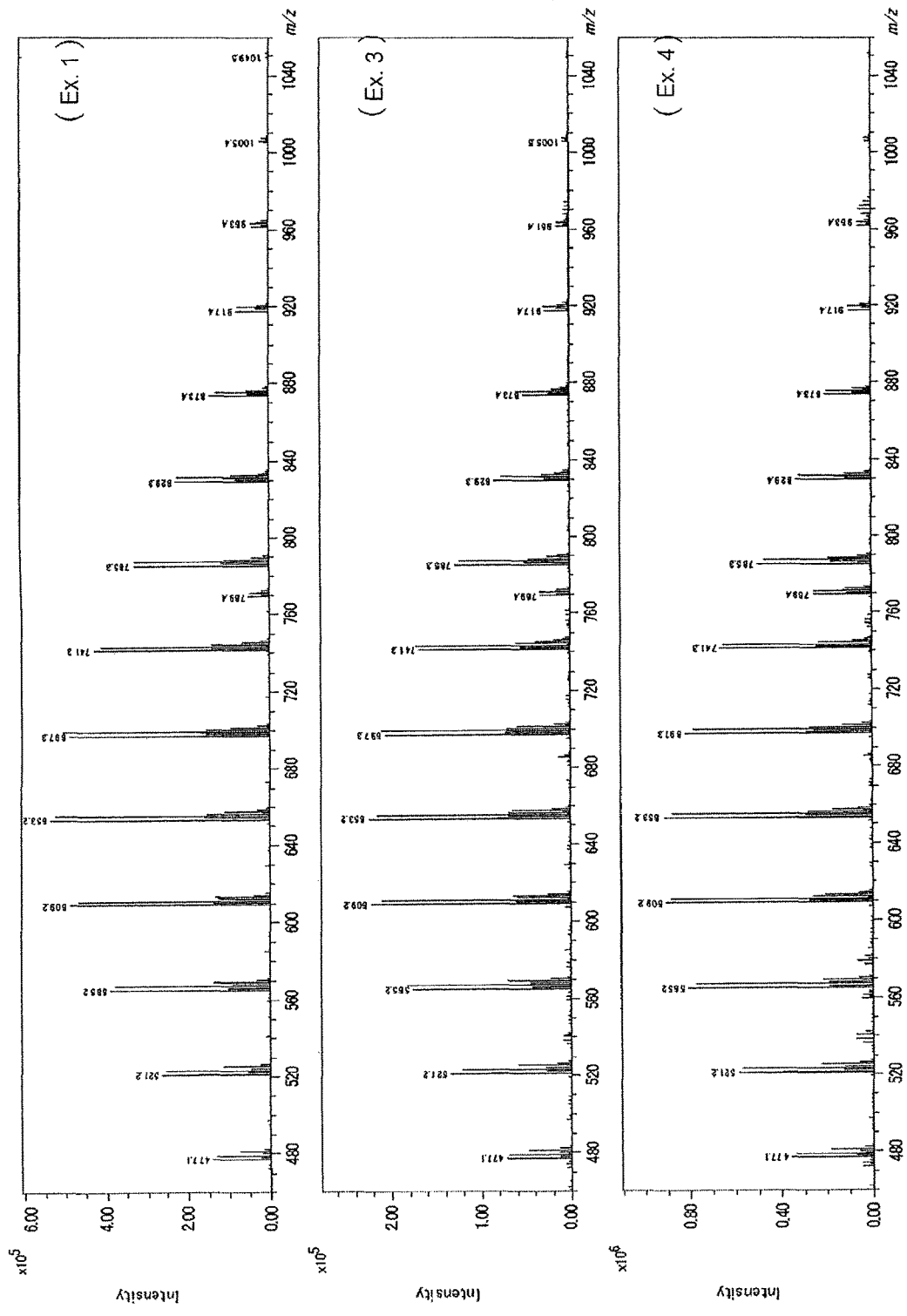
Figures 2, 4:
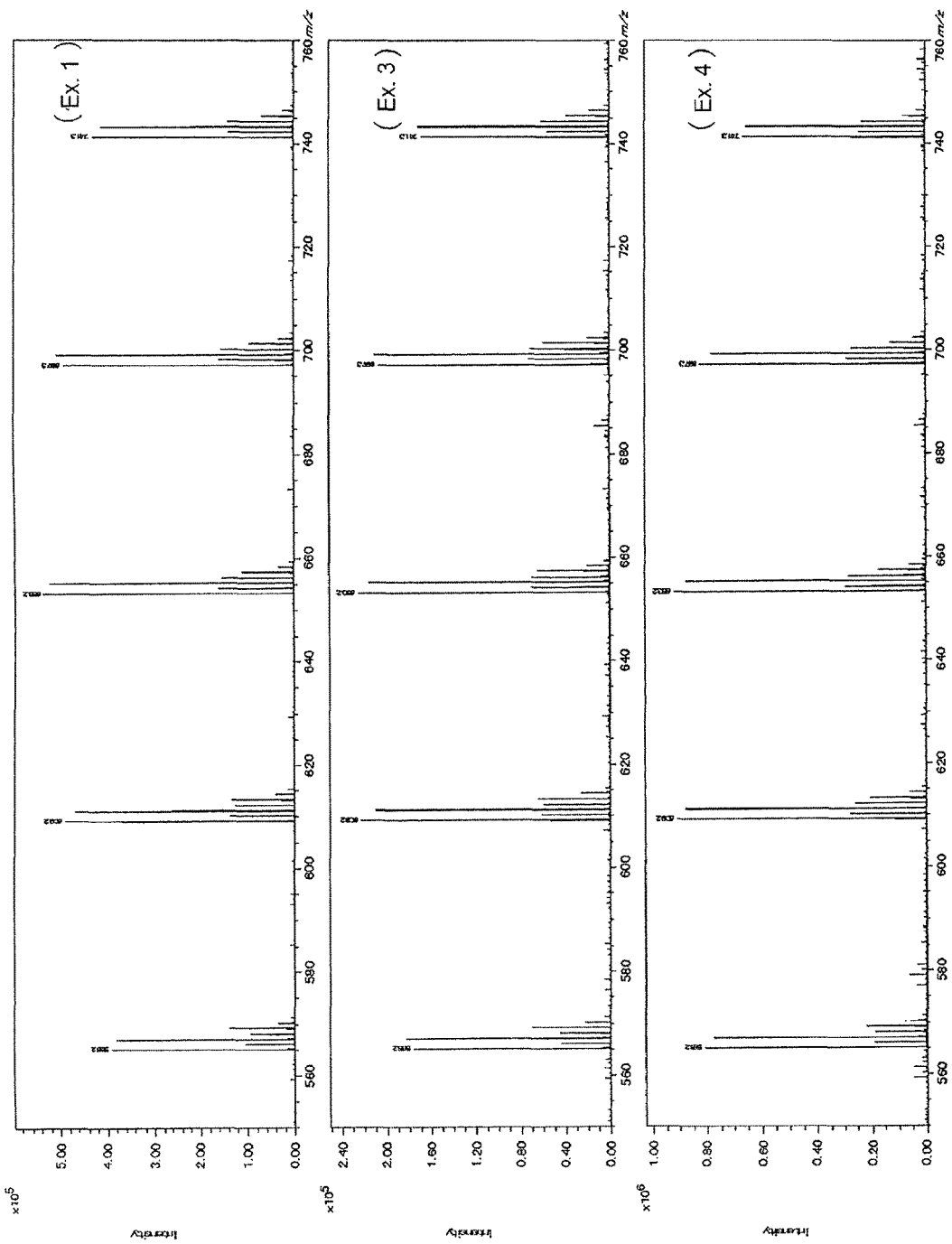

Mass spectrometric analysis was carried out in the same manner as in Ex. 1 except that the sample plate for mass spectrometric analysis in Ex. 3 was used. In the same manner as in Ex. 1, peaks derived from $Ag^+$-adduct sample molecules were observed at m/z of from 350 to 1,050. The mass spectrum at m/z of from 460 to 1,050 is shown in FIG. 4-1, and the mass spectrum in detail at m/z of from 550 to 750 is shown in FIG. 4-2, together with the mass spectrum in Ex. 1.

Ex. 4

A sample plate for mass spectrometric analysis was obtained in the same manner as in Ex. 3 except that the target as identified in Table 1 was used. $M_{Ag}$/Ag, O/Ag, the thickness of the metal thin film, the sheet resistance, the resistivity, the visible light transmittance, and the integrated intensity of a peak of $Ag3d_{5/2PL}$ where the integrated intensity of a peak derived from $Ag3d_{5/2}$ photoelectrons was 1, are shown in Table 1. Mass spectrometric analysis was performed in the same manner as in Ex. 1 and 3 except that the sample plate for mass spectrometric analysis in Ex. 4 was used. In the same manner as in Ex. 1 and 3, peaks derived from $Ag^+$-adduct sample molecules were observed at m/z of from 350 to 1,050. The mass spectrum at m/z of from 460 to 1,050 is shown in FIG. 4-1, and the mass spectrum in detail at m/z of from 550 to 750 is shown in FIG. 4-2, together with the mass spectra in Ex. 1 and 3.

Ex. 5

Figure 5:
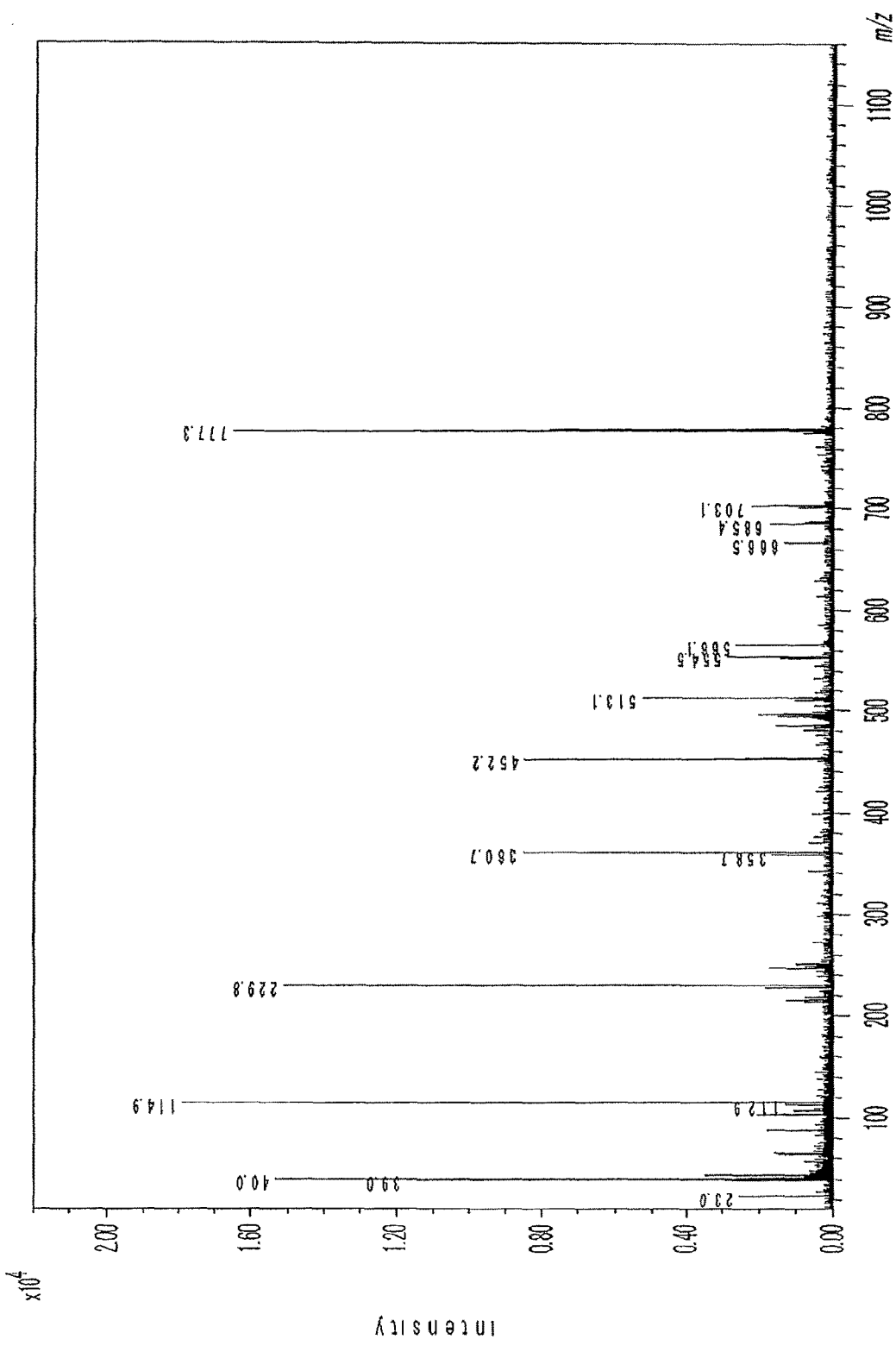
FIG. 5 is a mass spectrum within a range of m/z of from 0 to 1,100 obtained by mass spectrometric analysis using the sample plate for mass spectrometric analysis in Ex. 5.

An ITO film (thickness: 300 nm, sheet resistance: 8.0 Ω/sq.) was formed on the surface of a glass plate in the same manner as in Ex. 1 except that an ITO ($In_2O_3$/$SnO_2$: 95 wt %/5 wt %) target was used, a mixed gas of Ar and $O_2$ ($O_2$/Ar volume ratio=5/95) was used as a sputtering gas, and an electric power of 2 kw was applied, to prepare a sample plate for mass spectrometric analysis. Mass spectrometric analysis was performed in the same manner as in Ex. 1, 3 and 4 except that the sample plate for mass spectrometric analysis in Ex. 5 was used, however, no mass spectrum derived from sample molecules (at the intervals, Δm/z 44) was observed at m/z of from 350 to 1,050 (see FIG. 5).

TABLE 1

| | | Ex. 1 | Ex. 3 | Ex. 4 |
|---|---|---|---|---|
| Target | Main component | Ag | Ag | Ag |
| | Additive element | Au | Bi, Nd | Bi, Nd, Ge |
| | Ratio of additive element | 5 atomic % | Bi: 1 atomic % Nd: 0.2 atomic % | Bi: 1 atomic % Nd: 0.2 atomic % Ge: 1 atomic % |
| Metal thin film | $M_{Ag}$/Ag | 0.04 | Bi/Ag: 0.01 Nd/Ag: 0.002 | Bi/Ag: 0.01 Nd/Ag: 0.002 Ge/Ag: 0.01 |
| | O/Ag | n.d. | 0.08 | 0.09 |
| | Thickness of metal thin film (nm) | 14 | 10 | 8 |

TABLE 1-continued

| | Ex. 1 | Ex. 3 | Ex. 4 |
|---|---|---|---|
| Sheet resistance of metal thin film (Ω/sq.) | 6.4 | 9.6 | 16.4 |
| Resistivity of metal thin film (Ω · cm) | $9.0 \times 10^{-6}$ | $9.6 \times 10^{-6}$ | $1.3 \times 10^{-5}$ |
| Visible light transmittance of sample plate (%) | 53 | 61 | 68 |
| Peak intensity of $Ag3d_{5/2PL}$ | 0.07 | 0.06 | 0.05 |

Ex. 6

Figures 1, 6:
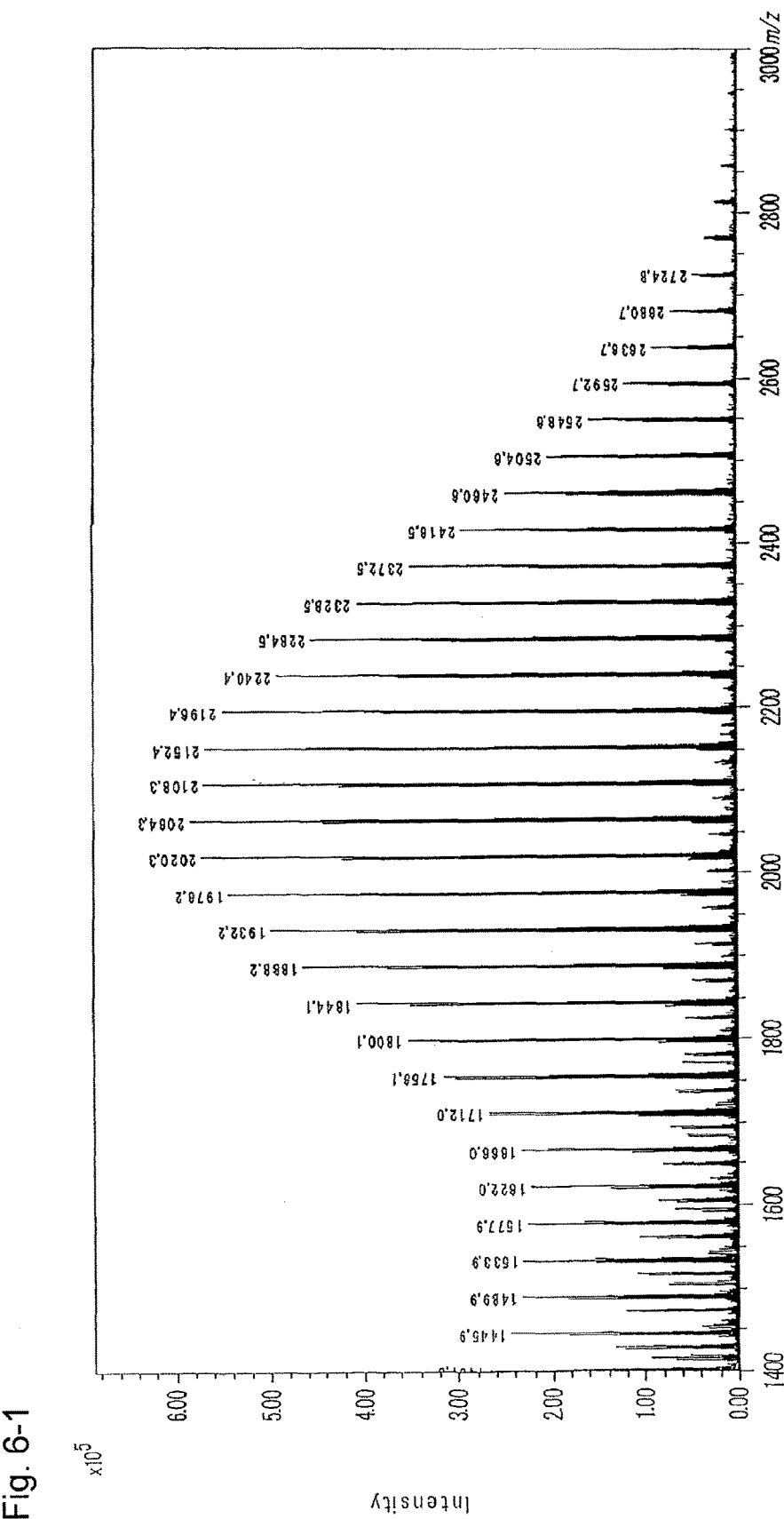
Figures 2, 6:
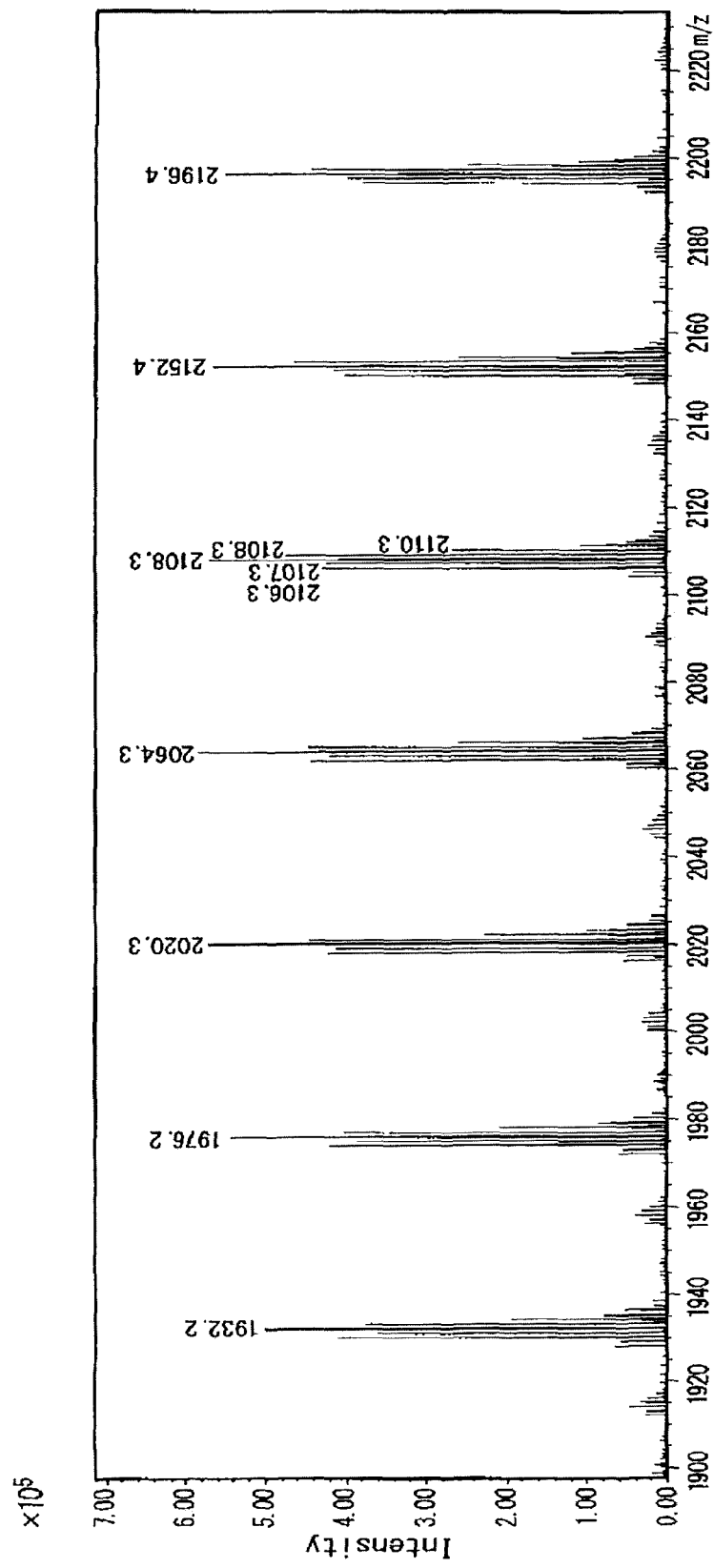

A sample plate for mass spectrometric analysis was obtained in the same manner as in Ex. 1 except that the target as identified in Table 2 was used. $M_{Ag}$/Ag, O/Ag, the thickness of the metal thin film, the sheet resistance, the resistivity, the visible light transmittance and the integrated intensity of a peak of $Ag3d_{5/2PL}$ where the integrated intensity of a peak derived from $Ag3d_{5/2}$ photoelectrons was 1, are shown in Table 2. Mass spectrometric analysis was performed in the same manner as in Ex. 1 except that the sample plate for mass spectrometric analysis in Ex. 6 and the sample solution (2) were used. Peaks derived from $Ag^+$-adduct sample molecules are observed at m/z of from 1,600 to 2,700 at the intervals, Δm/z 44 (derived from $CH_2CH_2O$) (see FIG. 6-1). Further, the mass spectrum in detail at m/z of from 1,900 to 2,230 is shown in FIG. 6-2.

$M_{Ag}$/Ag, O/Ag, the thickness of the metal thin film, the sheet resistance, the resistivity, the visible light transmittance, and the integrated intensity of a peak of $Ag3d_{5/2PL}$ where the integrated intensity of a peak derived from $Ag3d_{5/2}$ photoelectrons was 1, of the sample in Ex. 6, are shown in Table 2.

Ex. 7

Figure 7:
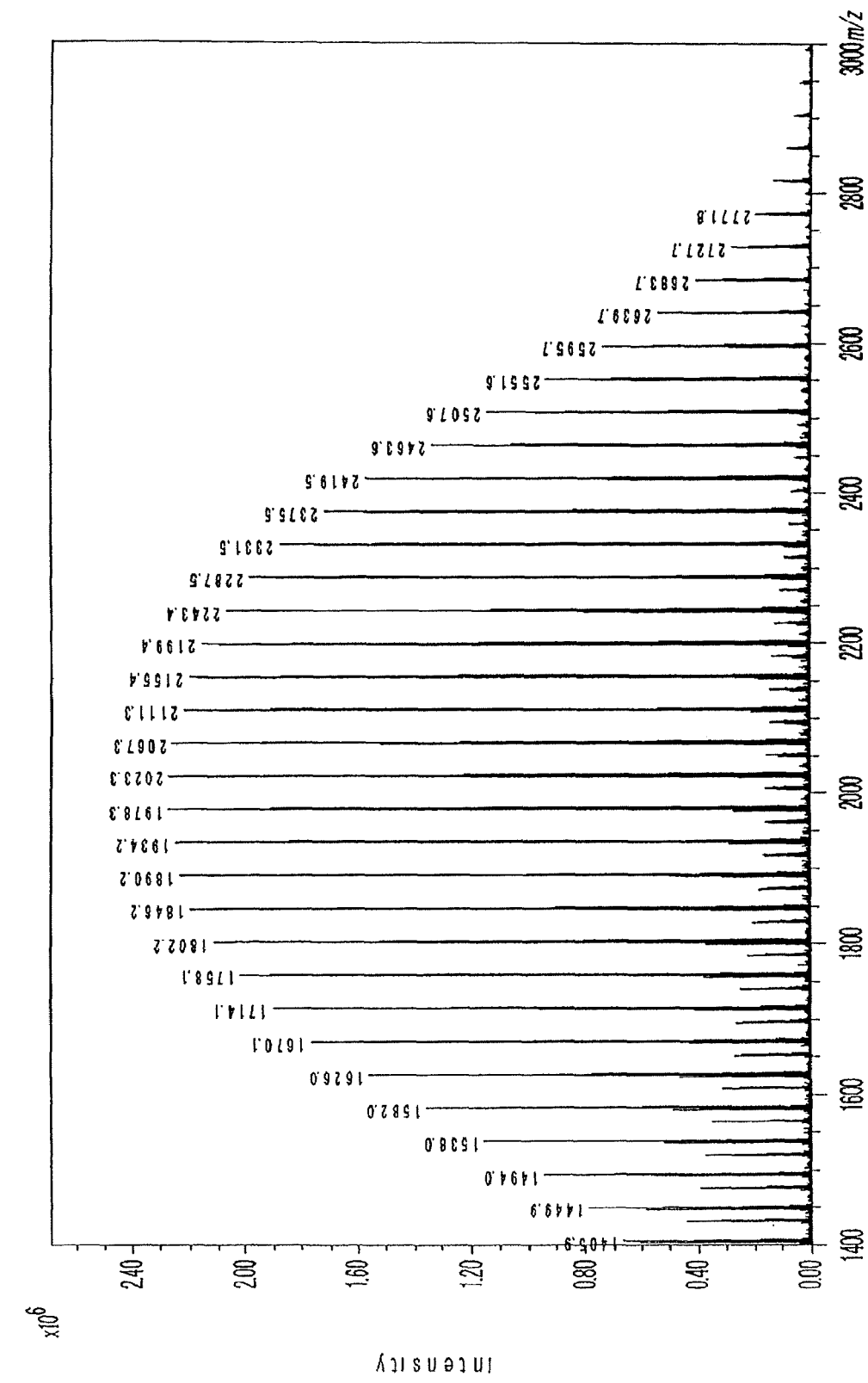
FIG. 7 is a mass spectrum obtained by mass spectrometric analysis using a matrix agent and a cationizing agent in combination, using the sample plate for mass spectrometric analysis in Ex. 7.

For reference, on the SUS target plate attached to the mass spectrometer, the sample solution (2) was directly dropped and dried, and further CHCA as a matrix agent and NaI as a cationizing agent were dropped and dried, and then mass spectrometric analysis was performed. The obtained mass spectrum is shown in FIG. 7 for reference.

Ex. 8

A PET film was placed in a vacuum chamber of a magnetron sputtering apparatus (manufactured by Nisshin Seiki, JVS-S03). The degree of vacuum in the vacuum chamber was adjusted to at most $8 \times 10^{-4}$ Pa, and high purity Ar gas (purity: 99.99 vol %) was introduced to adjust the degree of vacuum to $2 \times 10^{-1}$ Pa. A metal thin film (thickness: 13 nm) was formed on the surface of the PET film by using an Ag target (200 mm×70 mm) containing 1 atomic % of Cu, using an Ar gas as a sputtering gas and applying an electric power of 0.2 kw to prepare a sample plate for mass spectrometric analysis. $M_{Ag}$/Ag, O/Ag, the thickness of the metal thin film, the sheet resistance, the resistivity, the visible light transmittance and the integrated intensity of a peak of $Ag3d_{5/2PL}$ where the integrated intensity of a peak derived from $Ag3d_{5/2}$ photoelectrons was 1, are shown in Table 2.

Figure 8:
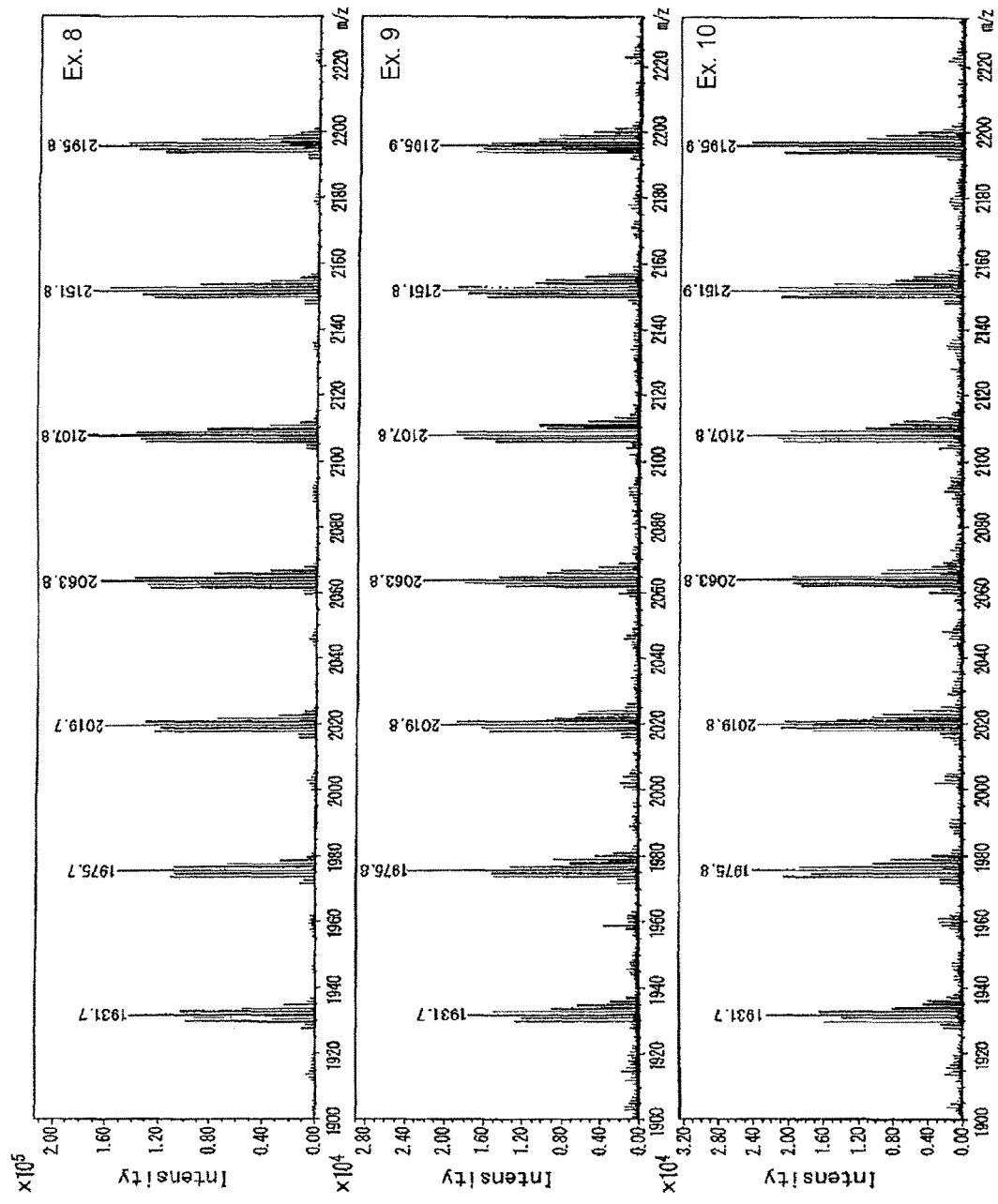
FIG. 8 is mass spectra obtained by mass spectrometric analysis using the sample plates for mass spectrometric analysis in Ex. 8 to 10.

Mass spectrometric analysis was carried out in the same manner as in Ex. 1 except that the sample plate for mass spectrometric analysis in Ex. 8 and the sample solution (2) were used. The mass spectrum in Ex. 8 obtained by mass spectrometric analysis is shown in FIG. 8.

Ex. 9 to Ex. 14

A sample plate for mass spectrometric analysis in each of Ex. 9 to 14 was obtained in the same manner as in Ex. 3 except that the target as identified in Table 2 or 3 was used. $M_{Ag}/Ag$, O/Ag, the thickness of the metal thin film, the sheet resistance, the resistivity, the visible light transmittance and the integrated intensity of a peak of $Ag3d_{5/2PL}$ where the integrated intensity of a peak derived from $Ag3d_{5/2}$ photoelectrons was 1, are shown in Table 2 or 3.

Figure 9:
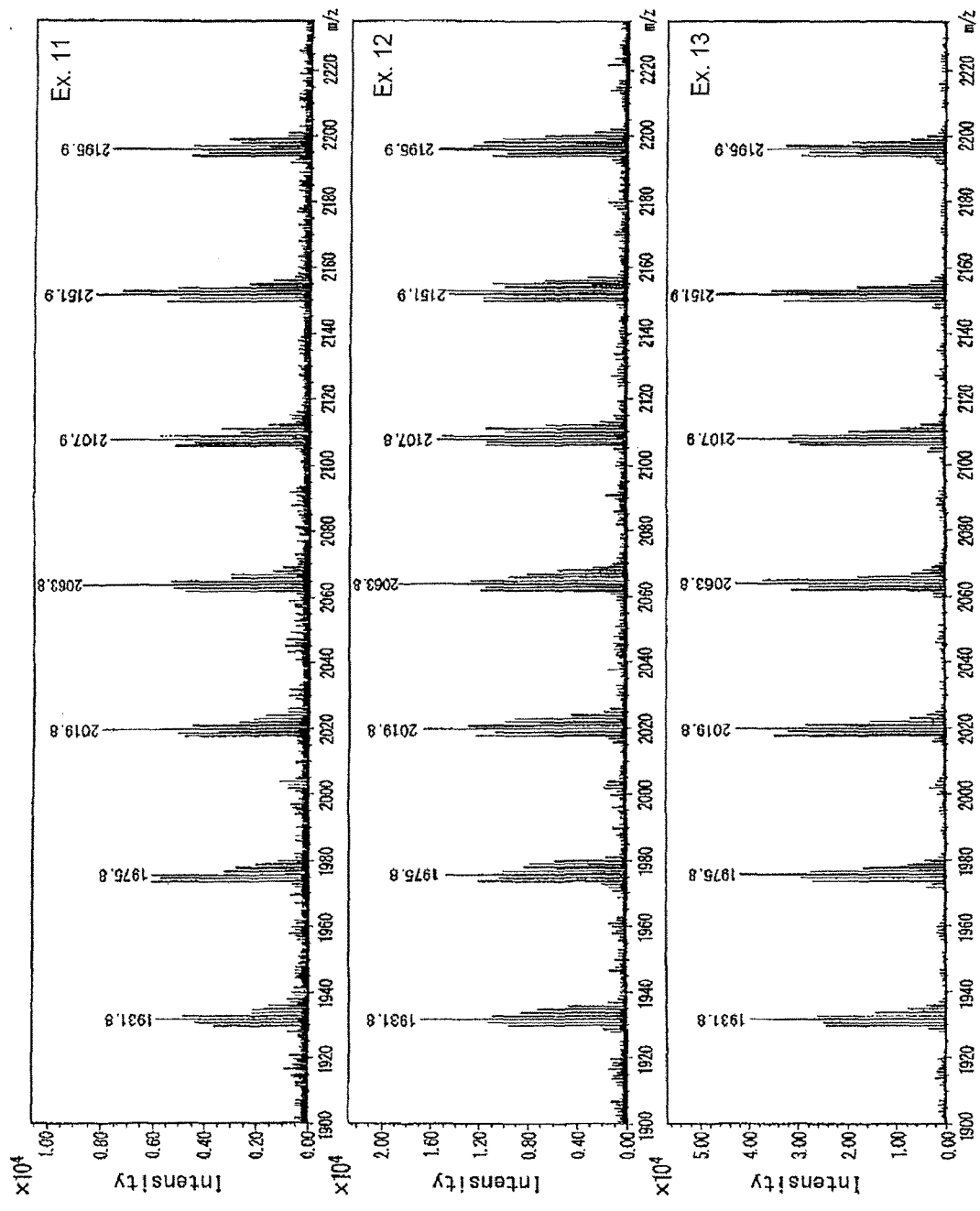
FIG. 9 is mass spectra obtained by mass spectrometric analysis using the sample plates for mass spectrometric analysis in Ex. 11 to 13.
Figure 10:
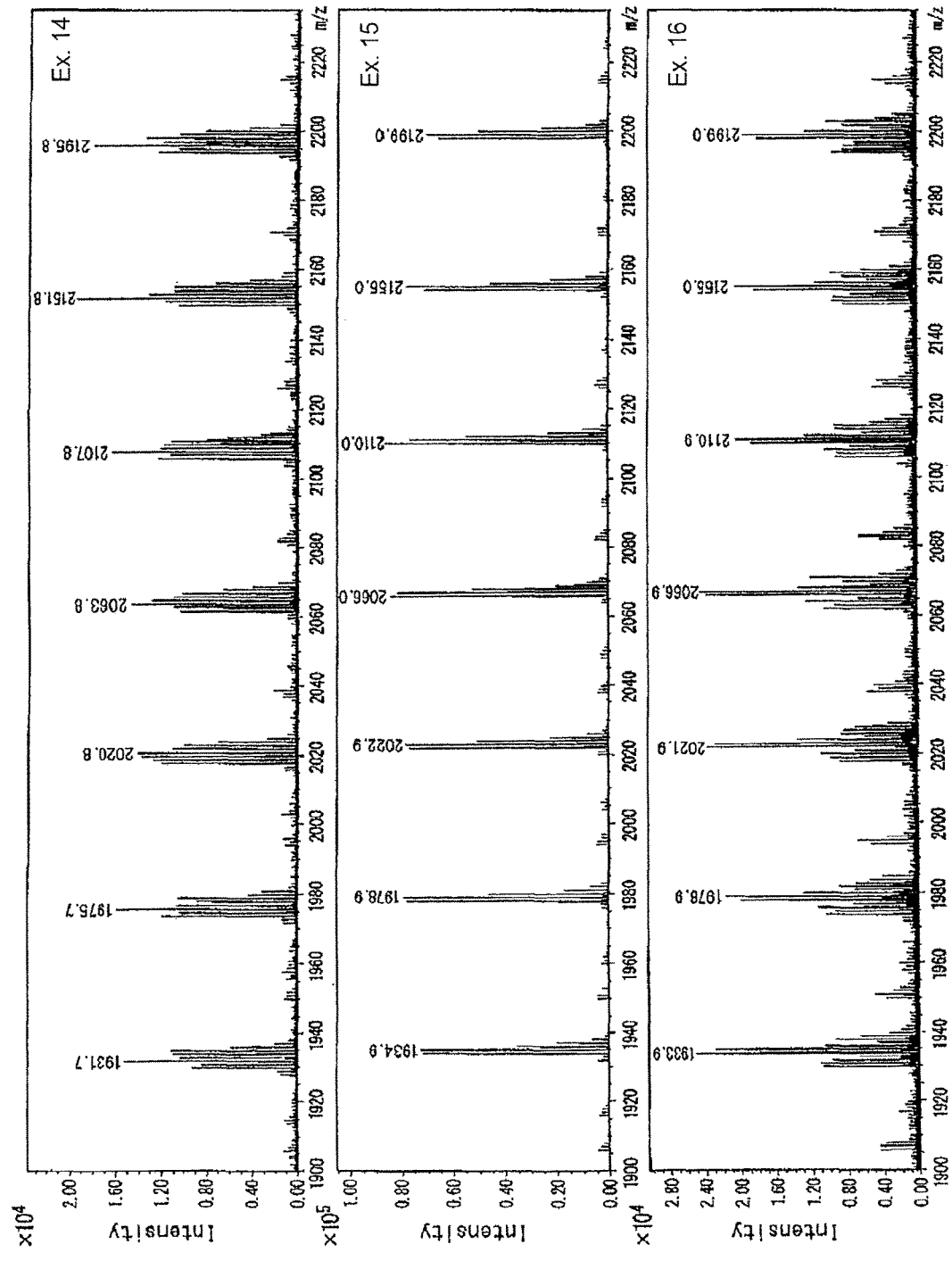
FIG. 10 is mass spectra obtained by mass spectrometric analysis using the sample plates for mass spectrometric analysis in Ex. 14 to 16.

Mass spectrometric analysis was performed in the same manner as in Ex. 1 except that the sample plate for mass spectrometric analysis in each of Ex. 9 to 14 and the sample solution (2) were used. The mass spectra in Ex. 9 to 14 obtained by mass spectrometric analysis are shown in FIGS. 8 to 10.

Ex. 15

A PET film was placed in a vacuum chamber of a magnetron sputtering apparatus (manufactured by BOC Industrial Gases, ILS-1600). The degree of vacuum in the vacuum chamber was adjusted to at most $1.3 \times 10^{-4}$ Pa, and high purity Ar gas (purity: 99.99 vol %) was introduced to adjust the degree of vacuum to $2 \times 10^{-1}$ Pa. A metal thin film (thickness: 20 nm) was formed on the surface of the PET film by using an Al target (432 mm×127 mm) comprising an Al—Mg—Si alloy (alloy No.: A6061), using an Ar gas as a sputtering gas and applying an electric power of 1 kw, to prepare a sample plate for mass spectrometric analysis. $M_{Al}/Al$, O/Al, the thickness of the metal thin film, the sheet resistance, the resistivity and the visible light transmittance are shown in Table 4.

Mass spectrometric analysis was performed in the same manner as in Ex. 1 except that the sample plate for mass spectrometric analysis in Ex. 15 and the sample solution (2) were used. The mass spectrum of Ex. 15 obtained by mass spectrometric analysis is shown in FIG. 10. A peak derived from $Na^+$ is observed at m/z of 23 and a peak derived from $Al^+$ is observed at m/z of 27, and peaks derived from $Na^+$-adduct sample molecules are observed at m/z of from 1,300 to 2,700.

Ex. 16

A PET film was placed in a vacuum chamber of a magnetron sputtering apparatus (manufactured by Nisshin Seiki, JVS-503). The degree of vacuum in the vacuum chamber was adjusted to at most $8 \times 10^{-4}$ Pa, and high purity Ar gas (purity: 99.99 vol %) was introduced to adjust the degree of vacuum to $2 \times 10^{-1}$ Pa. A metal thin film (thickness: 11 nm) was formed on the surface of the PET film by using a Cu target (200 mm×70 mm) comprising a Cu alloy with a ratio of the number of atoms of P to the number of atoms of Cu (P/Cu) of 0.001, using an Ar gas as a sputtering gas and applying an electric power of 0.2 kw to prepare a sample plate for mass spectrometric analysis. $M_{Cu}/Cu$ (P/Cu in this Ex.), O/Cu, the thickness of the metal thin film, the sheet resistance, the resistivity and the visible light transmittance are shown in Table 4.

Mass spectrometric analysis was performed in the same manner as in Ex. 1 except that the sample plate for mass spectrometric analysis in Ex. 16 and the sample solution (2) were used. The mass spectrum in Ex. 16 obtained by mass spectrometric analysis is shown in FIG. 10. A peak derived from $Na^+$ is observed at m/z of 23 and a peak derived from $Cu^+$ is observed at m/z of 63, and peaks derived from $Na^+$-adduct sample molecules and $Cu^+$-adduct sample molecules are observed at m/z of from 1,300 to 2,700.

Ex. 17

Figures 1, 11:
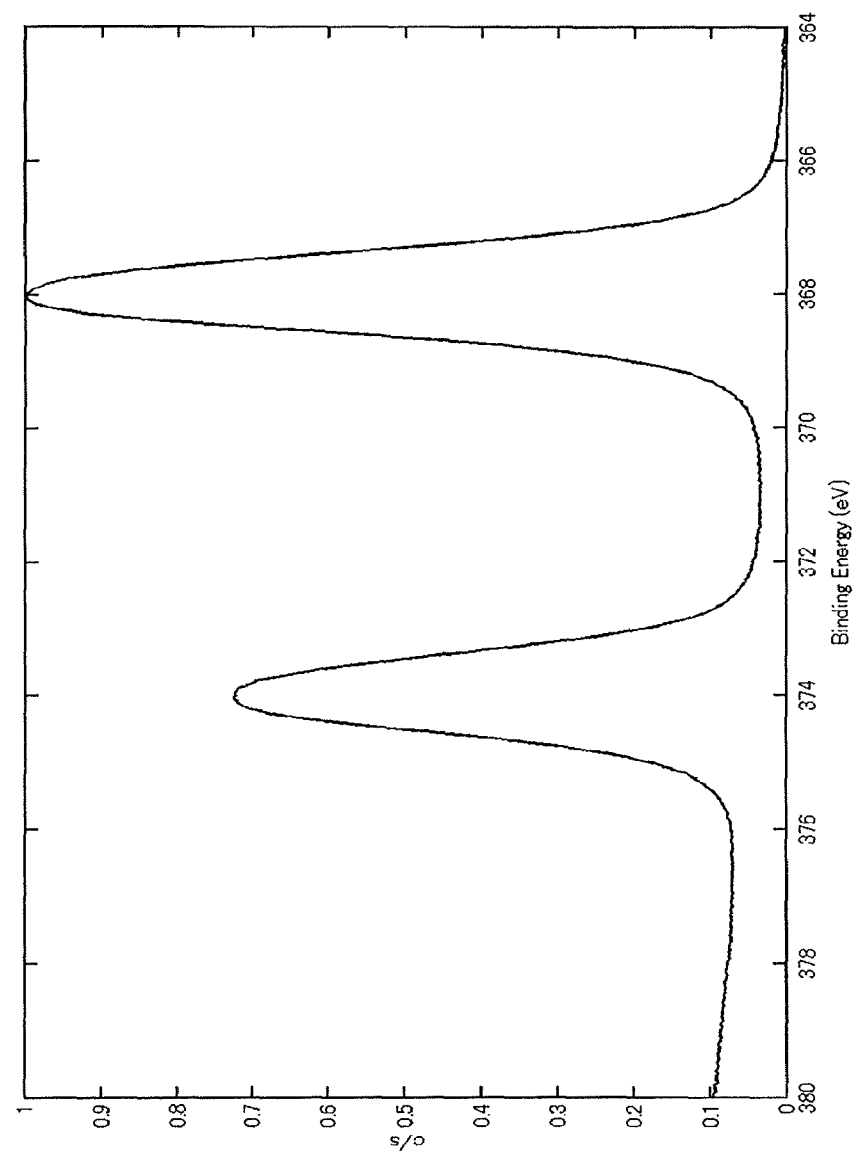
Figures 2, 11:
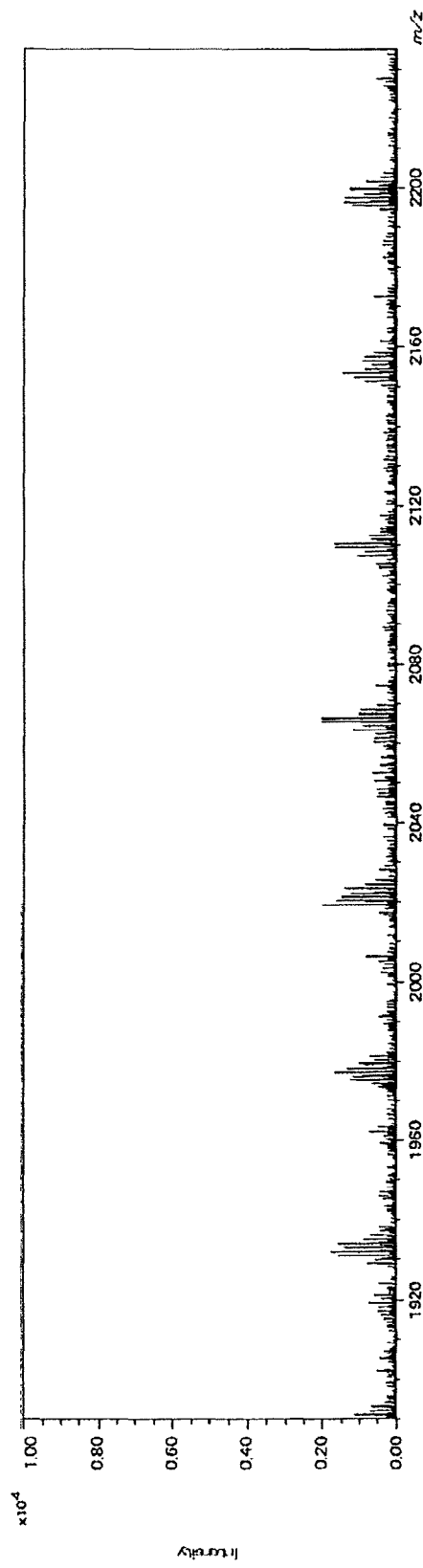

A glass plate was placed in a vacuum chamber of a magnetron sputtering apparatus (manufactured by Nisshin Seiki, JVS-S03), the degree of vacuum in the vacuum chamber was adjusted to at most $8 \times 10^{-4}$ Pa, and high purity Ar gas (purity: 99.99 vol %) was introduced to adjust the degree of vacuum to $2 \times 10^{-1}$ Pa. A metal thin film (thickness: 10 nm) was formed on the surface of the glass plate by using a Ag target (200 mm×70 mm) with purity of 4N, using an Ar gas as a sputtering gas and applying an electric power of 0.2 kw to prepare a Ag metal thin film-provided glass substrate, which was left in the air for one year, to prepare a sample plate for mass spectrometric analysis. Peaks derived from $Ag3d_{5/2}$ photoelectrons of the surface of the sample plate by X-ray photoelectron spectroscopy are shown in FIG. 11-1. No $Ag3d_{5/2PL}$ derived from surface plasmon was observed. Further, mass spectrometric analysis was performed in the same manner as in Ex. 1, however, no distinct mass spectrum was obtained (see FIG. 11-2).

TABLE 2

| | | Ex. 6 | Ex. 8 | Ex. 9 | Ex. 10 |
|---|---|---|---|---|---|
| Target | Main component | Ag | Ag | Ag | Ag |
| | Additive element | Au | Cu | Zr | Sn |
| | Ratio of additive element | 5 atomic % | 1 atomic % | 0.85 mass % | 5.5 mass % |
| Metal thin film | $M_{Ag}/Ag$ | 0.04 | 0.03 | 0.09 | 0.22 |
| | O/Ag | n.d. | n.d. | 0.16 | 0.06 |
| Thickness of metal thin film (nm) | | 7 | 13 | 15 | 11 |
| Sheet resistance of metal thin film (Ω/sq.) | | 12.4 | 5.3 | 6.1 | 15.2 |
| Resistivity of metal thin film (Ω · cm) | | $8.7 \times 10^{-6}$ | $6.9 \times 10^{-6}$ | $9.1 \times 10^{-6}$ | $1.6 \times 10^{-5}$ |
| Visible light transmittance of sample plate (%) | | 68 | 50 | 51 | 51 |
| Peak intensity of $Ag3d_{5/2PL}$ | | 0.07 | 0.05 | 0.04 | 0.06 |

TABLE 3

| | | Ex. 11 | Ex. 12 | Ex. 13 | Ex. 14 |
|---|---|---|---|---|---|
| Target | Main component | Ag | Ag | Ag | Ag |
| | Additive element | Cr | Ti | Co | Pd |
| | Ratio of additive element | 0.49 mass % | 0.45 mass % | 0.55 mass % | 10 mass % |
| Metal thin film | $M_{Ag}/Ag$ | — | 0.02 | 0.04 | 0.08 |
| | O/Ag | 0.03 | 0.05 | n.d. | — |
| Thickness of metal thin film (nm) | | 13 | 13 | 15 | 9 |
| Sheet resistance of metal thin film (Ω/sq.) | | 4.6 | 5.8 | 7.4 | 18 |
| Resistivity of metal thin film (Ω · cm) | | $6.0 \times 10^{-6}$ | $7.5 \times 10^{-6}$ | $1.1 \times 10^{-5}$ | $1.6 \times 10^{-5}$ |
| Visible light transmittance of sample plate (%) | | 49 | 51 | 52 | 49 |
| Peak intensity of $Ag3d_{5/2PL}$ | | 0.07 | 0.08 | 0.07 | 0.06 |

TABLE 4

|  |  | Ex. 15 | Ex. 16 |
|---|---|---|---|
| Target | Type | Al—Mg—Si alloy (A6061) | Cu alloy |
|  | Additive element and its ratio | Mg: 0.8-1.2%<br>Si: 0.4-0.8%<br>Cu: 0.15-4.0%<br>Cr: 0.04-0.35% | P/Cu: 0.001 |
| Metal thin film | $M_{Al}$/Al, $M_{Cu}$/Cu<br>O/Al, O/Cu | Mg/Al: 0.07<br>1.48 | P/Cu: n.d.<br>0.08 |
|  | Thickness of metal thin film (nm) | 20 | 11 |
|  | Sheet resistance of metal thin film (Ω/sq.) | 7.6 | 21.8 |
|  | Resistivity of metal thin film (Ω · cm) | $1.5 \times 10^{-5}$ | $2.4 \times 10^{-5}$ |
|  | Visible light transmittance of sample plate (%) | 7 | 53 |

In Table 4, 1.48 in the row of the metal thin film in Ex. 15 represents the O/Al value, and 0.08 in the row of the metal thin film in Ex. 16 represents the O/Cu value.

In Tables 1 to 4, "n.d." represents the detection lower limit or lower in X-ray photoelectron spectroscopy. With respect to a trace amount of Cr in the metal thin film in Ex. 11, the composition cannot be calculated since the binding energy positions of Cr2p and Ag3p$_{3/2}$ as main peaks overlap with each other, and the value of $M_{Ag}$/Ag is represented as "-". In Table 3, with respect to a trace amount of O in the metal thin film in Ex. 14, the composition cannot be calculated since the binding energy positions of O1s and Pd3p$_{3/2}$ as main peaks overlap with each other, and the value of O/Ag is represented as "-". In Table 4, the amounts of Si, Cu and Cr in the metal thin film in Ex. 15 are at most the detection lower limit in X-ray photoelectron spectroscopy, and only the Mg/Al value is shown.

Ex. 18, 19 and 22

In Ex. 18, 19 and 22, the same sample plates for mass spectrometric analysis as in Ex. 6, 14 and 12, respectively, were prepared. $M_{Ag}$/Ag, O/Ag, the thickness of the metal thin film, the sheet resistance, the resistivity and the visible light transmittance are shown in Table 5.

Figure 12:
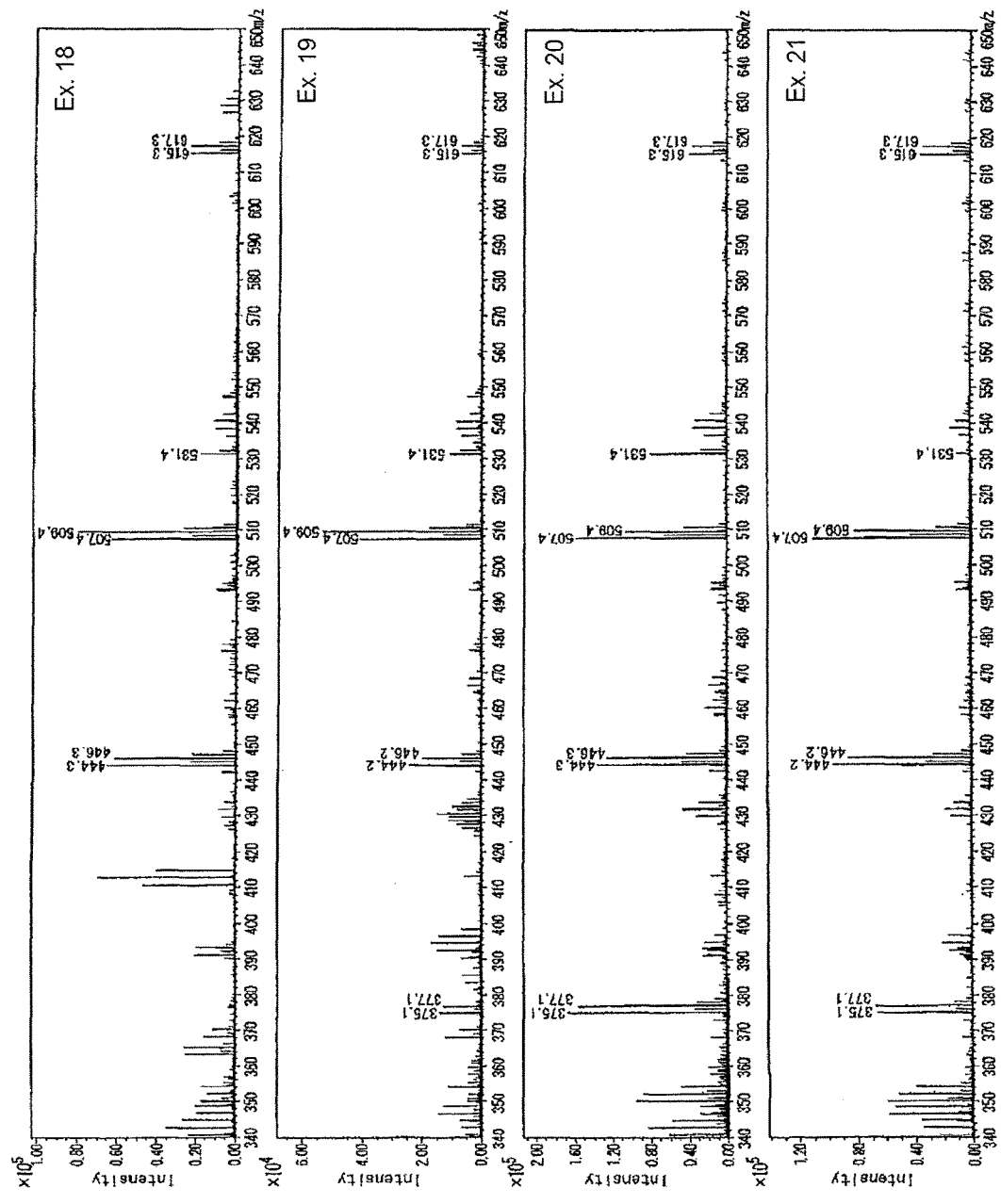
FIG. 12 is mass spectra obtained by mass spectrometric analysis using the sample plates for mass spectrometric analysis in Ex. 18 to 21.
Figure 13:
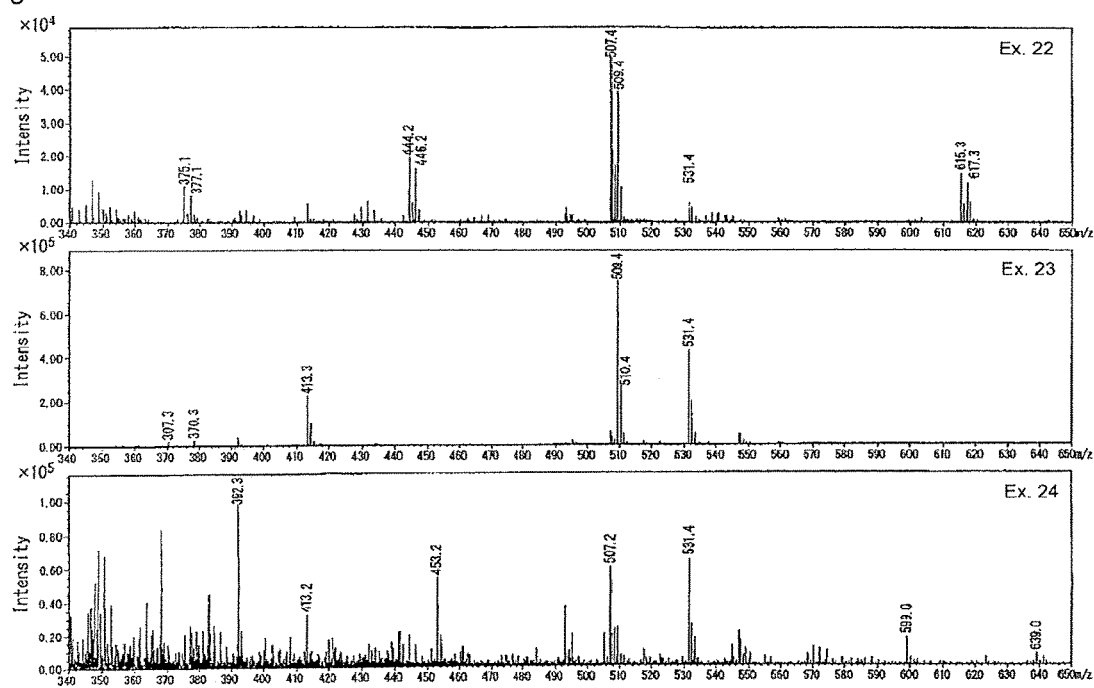
FIG. 13 is mass spectra obtained by mass spectrometric analysis using the sample plates for mass spectrometric analysis in Ex. 22 to 24.

Mass spectrometric analysis was performed in the same manner as in Ex. 1 except that the sample solution (3) was used. The mass spectra in Ex. 18, 19 and 22 obtained by mass spectrometric analysis are shown in FIGS. 12 and 13. Peaks derived from Ag$^+$ are observed at m/z of 107 and m/z of 109, and peaks derived from Ag$^+$-adduct sample molecules are observed at m/z of 615 and 617.

Ex. 20 and 21

Sample plates for mass spectrometric analysis in Ex. 20 and 21 were obtained in the same manner as in Ex. 3 except that the target shown in Table 5 was used. $M_{Ag}$/Ag, O/Ag, the thickness of the metal thin film, the sheet resistance, the resistivity and the visible light transmittance are shown in Table 5.

Mass spectrometric analysis was performed in the same manner as in Ex. 1 except that the sample plate for mass spectrometric analysis in each of Ex. 20 and 21 and the sample solution (3) were used. The mass spectra of Ex. 20 and 21 obtained by mass spectrometric analysis are shown in FIG. 12.

Ex. 23

The same sample plate for mass spectrometric analysis as in Ex. 15 was prepared. $M_{Al}$/Al, O/Al, the thickness of the metal thin film, the sheet resistance, the resistivity and the visible light transmittance are shown in Table 6.

Mass spectrometric analysis was performed in the same manner as in Ex. 1 except that the sample plate for mass spectrometric analysis in Ex. 23 and the sample solution (3) were used. The mass spectrum in Ex. 23 obtained by mass spectrometric analysis is shown in FIG. 13.

Ex. 24

The same sample plate for mass spectrometric analysis as in Ex. 16 was prepared. $M_{Cu}$/Cu (P/Cu in this Ex.), O/Cu, the thickness of the metal thin film, the sheet resistance, the resistivity and the visible light transmittance are shown in Table 6.

Mass spectrometric analysis was performed in the same manner as in Ex. 1 except that the sample plate for mass spectrometric analysis in Ex. 24 and the sample solution (3) were used. The mass spectrum in Ex. 24 obtained by mass spectrometric analysis is shown in FIG. 13.

TABLE 5

|  |  | Ex. 18 | Ex. 19 | Ex. 20 | Ex. 21 | Ex. 22 |
|---|---|---|---|---|---|---|
| Target | Main component | Ag | Ag | Ag | Ag | Ag |
|  | Additive element | Au | Pd | Ni | Si | Ti |
|  | Ratio of additive element | 5 atomic % | 10 mass % | 7.8 mass % | 1 atomic % | 0.45 mass % |
| Metal thin film | $M_{Ag}$/Ag | 0.04 | 0.08 | 0.20 | 0.02 | 0.02 |
|  | O/Ag | n.d. | — | 0.05 | 0.01 | 0.05 |
| Thickness of metal thin film (nm) |  | 7 | 9 | 10 | 14 | 13 |
| Sheet resistance of metal thin film (Ω/sq.) |  | 12.4 | 18 | 23.8 | 5.6 | 5.8 |
| Resistivity of metal thin film (Ω · cm) |  | $8.7 \times 10^{-6}$ | $1.6 \times 10^{-5}$ | $2.5 \times 10^{-5}$ | $7.6 \times 10^{-6}$ | $7.5 \times 10^{-6}$ |
| Visible light transmittance of sample plate (%) |  | 68 | 49 | 47 | 51 | 51 |

TABLE 6

|  |  | Ex. 23 | Ex. 24 |
|---|---|---|---|
| Target | Type | Al—Mg—Si alloy (A6061) | Cu alloy |
|  | Additive element and its ratio | Mg: 0.8-1.2%<br>Si: 0.4-0.8%<br>Cu: 0.15-4.0%<br>Cr: 0.04-0.35% | P/Cu: 0.001 |
| Metal thin film | $M_{Al}$/Al, $M_{Cu}$/Cu<br>O/Al, O/Cu | Mg/Al: 0.07<br>1.48 | P/Cu: n.d.<br>0.08 |
|  | Thickness of metal thin film (nm) | 20 | 11 |
|  | Sheet resistance of metal thin film (Ω/sq.) | 7.6 | 21.8 |
|  | Resistivity of metal thin film (Ω · cm) | $1.5 \times 10^{-5}$ | $2.4 \times 10^{-5}$ |
|  | Visible light transmittance of sample plate (%) | 7 | 53 |

In Table 6, 1.48 in the row of the metal thin film in Ex. 23 represents the O/Al value, and 0.08 in the row of the metal thin film in Ex. 24 represents the O/Cu value.

In Tables 5 and 6, "n.d." represents the detection lower limit or lower by X-ray photoelectron spectroscopy. In Table 5, with respect to a trace amount of O in the metal thin film in Ex. 19, the composition cannot be calculated since the binding energy positions of O1s and Pd3p$_{3/2}$ as main peaks overlap with each other, and the O/Ag value is represented as "-".

INDUSTRIAL APPLICABILITY

The sample plate for mass spectrometric analysis of the present invention is useful as a sample plate for mass spectrometric analysis used when IMS is conducted by LDI-MS.

This application is a continuation of PCT Application No. PCT/JP2016/063676, filed on May 6, 2016, which is based upon and claims the benefit of priority from Japanese Patent Application No. 2015-095363 filed on May 8, 2015. The contents of those applications are incorporated herein by reference in their entireties.

REFERENCE SYMBOLS

10: Sample plate for mass spectrometric analysis
12: Substrate
14: Metal thin film

What is claimed is:
What is claimed is:

1. A sample plate for mass spectrometric analysis, which comprises a substrate and a metal thin film formed on the substrate, wherein a surface of the metal thin film opposite to a substrate side is an outermost surface, wherein the metal thin film is selected from the group consisting of the following (A), (B), and (C):
   (A) a metal thin film containing Ag and at least one additive element $M_{Ag}$ selected from the group consisting of Pd, Au, Pt, Ir, Cu, Al, Zn, Sn, Ni, Cr, Co, Zr, Si, Ti, Sb, Ga, Nd, Ge and Bi, wherein a ratio $M_{Ag}$/Ag of the total number of atoms of the additive element $M_{Ag}$ to the number of atoms of Ag in the metal thin film is from 0.001 to 0.5;
   (B) a metal thin film containing Al and at least one additive element $M_{Al}$ selected from the group consisting of Nd, Cu, Si, Mg, Cr, Mn, Zn, Fe, Ta, Ni, La, Ge, Ga, Ag, Au, Pd, Pt, Ir and Ti, wherein a ratio $M_{Al}$/Al of the total number of atoms of the additive element $M_{Al}$ to the number of atoms of Al in the metal thin film is from 0.001 to 0.5; and
   (C) a metal thin film containing Cu and at least one additive element $M_{Cu}$ selected from the group consisting of Sn, Zn, Pb, Ni, Al, Fe, Mn, Au, Ti, Cr, Mg, Si, In, Ga, Se, Ca, Ag, Au, Pd, Pt, Ir and P, wherein a ratio $M_{Cu}$/Cu of the total number of atoms of the additive element $M_{Cu}$ to the number of atoms of Cu in the metal thin film is from 0.001 to 0.5,
   wherein the metal thin film is deposited or sputtered and a thickness of the metal thin film is from 0.1 to 20 nm, and
   wherein the sample plate does not contain concave-convex structures, nanostructures, and microstructures formed on its surface.

2. The sample plate according to claim 1, wherein the sample plate comprises the metal thin film (A), wherein the metal thin film (A) comprises a number of oxygen (O) atoms, and wherein a ratio O/Ag of the number of O atoms to the number of Ag atoms in the metal thin film (A) is from 0 to 0.2.

3. The sample plate according to claim 2, wherein the ratio O/Ag of the number of O atoms to the number of Ag atoms in the metal thin film (A) is from 0.05 to 0.2.

4. The sample plate according to claim 1, wherein the sample plate comprises the metal thin film (A), and resistivity of the metal thin film (A) is at most $1\times10^{-4}$ Ω·cm.

5. The sample plate according to claim 1, wherein in an X-ray photoelectron spectrum of the surface of the metal thin film (A) obtained by X-ray photoelectron spectroscopy, integrated intensity of a peak observed at a binding energy position higher by from 2.5 to 5 eV than the position 368 eV of a peak derived from Ag3d$_{5/2}$ photoelectrons, is higher than 0.001, wherein the integrated intensity of the peak derived from Ag3d$_{5/2}$ photoelectrons is 1.

6. The sample plate according to claim 1, wherein the sample plate comprises the metal thin film (B), wherein the metal thin film (B) comprises a number of oxygen (O) atoms, and wherein a ratio O/Al of the number of O atoms to the number of Al atoms in the metal thin film (B) is from 0 to 1.5.

7. The sample plate according to claim 6, wherein the ratio O/Al of the number of O atoms to the number of Al atoms in the metal thin film (B) is from 0.5 to 1.5.

8. The sample plate according to claim 1, wherein the sample plate comprises the metal thin film (B), and resistivity of the metal thin film (B) is at most $1\times10^{-3}$ Ω·cm.

9. The sample plate according to claim 1, wherein in an X-ray photoelectron spectrum of the surface of the metal thin film (B) obtained by X-ray photoelectron spectroscopy, integrated intensity of a peak observed at a binding energy position higher by from 5 to 43 eV than the position 73 eV of a peak derived from Al2p$_{3/2}$ photoelectrons, is higher than 0.01, where the integrated intensity of the peak derived from Al2p$_{3/2}$ photoelectrons is 1.

10. The sample plate according to claim 1, wherein the sample plate comprises the metal thin film (C), wherein the metal thin film (C) comprises a number of oxygen (O) atoms, and wherein a ratio O/Cu of the number of O atoms to the number of Cu atoms in the metal thin film (C) is from 0 to 0.3.

11. The sample plate according to claim 10, wherein the ratio O/Cu of the number of O atoms to the number of Cu atoms in the metal thin film (C) is from 0.1 to 0.3.

12. The sample plate for mass spectrometric analysis according to claim 1, wherein the sample plate comprises the metal thin film (C), and resistivity of the metal thin film (C) is at most $1\times10^{-3}$ Ω·cm.

13. A mass spectrometric analysis method, comprising providing the sample plate of claim 1, placing a sample on the surface of the metal thin film of the sample plate, and conducting a mass spectrometric analysis.

14. A mass spectrometric analysis device, which is provided with the sample plate for mass spectrometric analysis as defined in claim 1.

* * * * *